(12) United States Patent
Maeta

(10) Patent No.: US 10,872,694 B2
(45) Date of Patent: Dec. 22, 2020

(54) SOFTWARE, HEALTH CONDITION DETERMINATION APPARATUS, AND HEALTH CONDITION DETERMINATION METHOD

(71) Applicant: MAEDA SHOUJI CO., LTD., Fukuoka (JP)

(72) Inventor: Shunsuke Maeta, Fukuoka (JP)

(73) Assignee: MAEDA SHOUJI CO., LTD., Fukuoka (JP)

( * ) Notice: Subject to any disclaimer, the term of this patent is extended or adjusted under 35 U.S.C. 154(b) by 231 days.

(21) Appl. No.: 16/313,429

(22) PCT Filed: Apr. 3, 2017

(86) PCT No.: PCT/JP2017/013923
§ 371 (c)(1),
(2) Date: Dec. 26, 2018

(87) PCT Pub. No.: WO2018/185808
PCT Pub. Date: Oct. 11, 2018

(65) Prior Publication Data
US 2019/0228860 A1   Jul. 25, 2019

(51) Int. Cl.
*G16H 40/63*   (2018.01)
*G16H 50/20*   (2018.01)
(Continued)

(52) U.S. Cl.
CPC ............. *G16H 40/63* (2018.01); *G06Q 50/22* (2013.01); *G16H 50/20* (2018.01); *G06F 17/18* (2013.01)

(58) Field of Classification Search
CPC ........ G16H 40/63; G16H 50/20; G06Q 50/22; G06F 17/18
(Continued)

(56) References Cited

U.S. PATENT DOCUMENTS

| | | | |
|---|---|---|---|
| 6,579,231 B1* | 6/2003 | Phipps ................. | A61B 5/0002 128/903 |
| 6,605,038 B1* | 8/2003 | Teller .................... | G16H 20/70 600/300 |

(Continued)

FOREIGN PATENT DOCUMENTS

| | | |
|---|---|---|
| JP | 2007-535357 A | 12/2007 |
| JP | 2011-150395 A | 8/2011 |

(Continued)

*Primary Examiner* — Joy Chng
(74) *Attorney, Agent, or Firm* — Heedong Chae; Lucem, PC

(57) ABSTRACT

A health conditioin determination apparatus 1, which is an example of a health condition determination employing the present invention, is provided with an operation unit 2. The operation unit 2 is a processing unit for implementing each information processing function of the health condition determination apparatus 1. In other words, a software employing the present invention allows an operation unit 2 of a tablet terminal 3 to function as an information input unit 23, an information recording unit 24, a standard calculation unit 5, and a determination processing unit 6. The present invention performs the transmission and reception of information, the recording of information, the determination of normality or abnormality, the setting of a determination standard, the notice of determination results, the creation or display of display information, and the like, by the processing function of each of the units.

24 Claims, 17 Drawing Sheets

(51) Int. Cl.
*G06Q 50/22* (2018.01)
*G06F 17/18* (2006.01)

(58) Field of Classification Search
USPC .......................................................... 705/2–3
See application file for complete search history.

(56) References Cited

U.S. PATENT DOCUMENTS

| | | | | |
|---|---|---|---|---|
| 7,772,965 B2* | 8/2010 | Farhan | ................... | G16H 40/63 |
| | | | | 340/286.07 |
| 9,044,136 B2* | 6/2015 | Luo | ...................... | A61B 5/4815 |
| 2006/0252999 A1* | 11/2006 | Devaul | ................... | A61B 5/411 |
| | | | | 600/300 |
| 2016/0026354 A1* | 1/2016 | McIntosh | ............... | G16H 40/67 |
| | | | | 706/12 |

FOREIGN PATENT DOCUMENTS

| | | | |
|---|---|---|---|
| JP | 2012-065713 A | 4/2012 | |
| JP | 2013-183810 A | 9/2013 | |
| JP | 2016-085478 A | 5/2016 | |
| JP | 2017-000455 A | 1/2017 | |
| JP | 2017-023560 A | 2/2017 | |
| JP | 2017-042386 A | 3/2017 | |
| WO | WO-2010135518 A1 * | 11/2010 | ......... A61B 5/02055 |

* cited by examiner

| Staff | |
|---|---|
| User | |

| Items | Measurement data | | | |
|---|---|---|---|---|
| Body temperature | °C | 7 | 8 | 9 |
| Systolic blood pressure | mmHg | 4 | 5 | 6 |
| Diastolic blood pressure | mmHg | 1 | 2 | 3 |
| Pulse | bpm | 0 | . | C |
| Oxygen concentration | % | | | |
| Body weight | Kg | | | |
| Respiration | Times of breats | | | |
| Meals | ○ Normal ○ Abnormal | | Transmit | |
| Urination | ○ Normal ○ Abnormal | | | |
| Defecation | ○ Normal ○ Abnormal | | | |
| Observation・Inquiries | ○ Normal ○ Abnormal [Comment] | | Close | |

Please authentify staff card

(a)
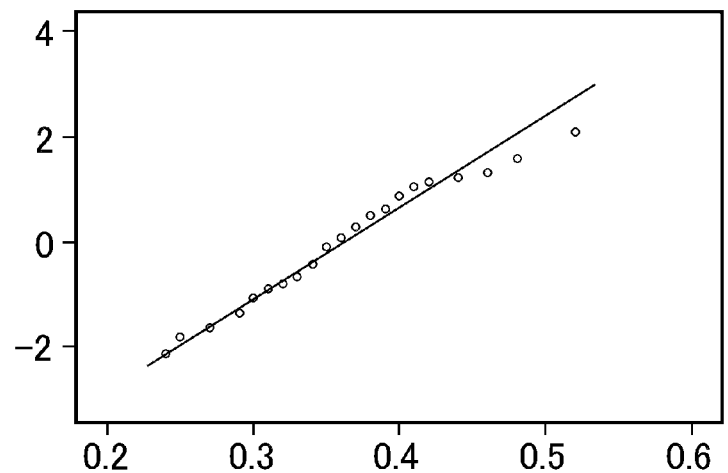
(b)
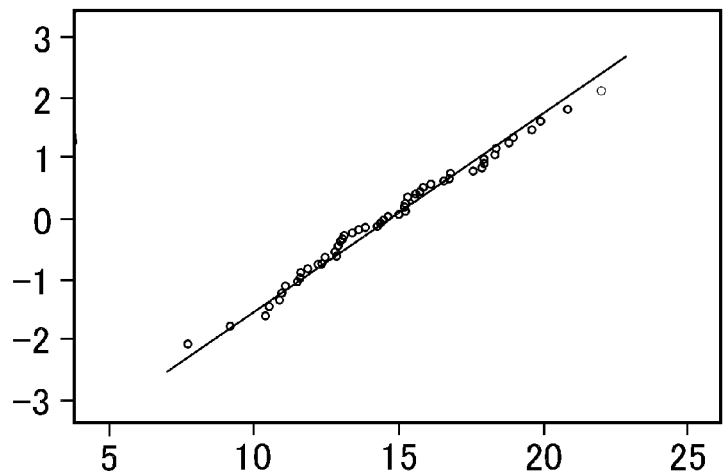
FIG.12

(a)
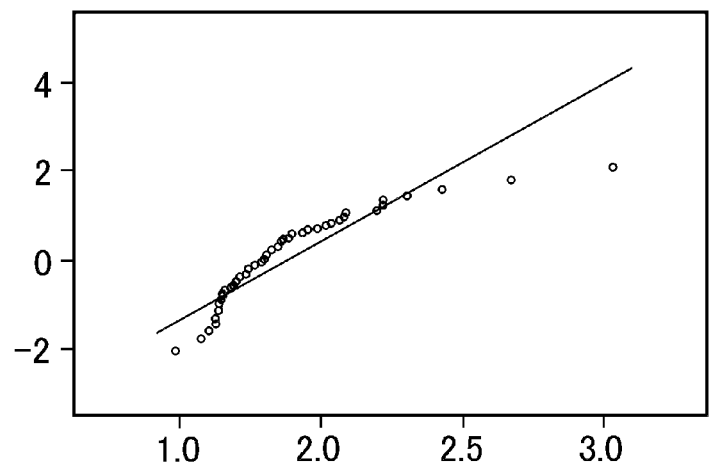
(b)
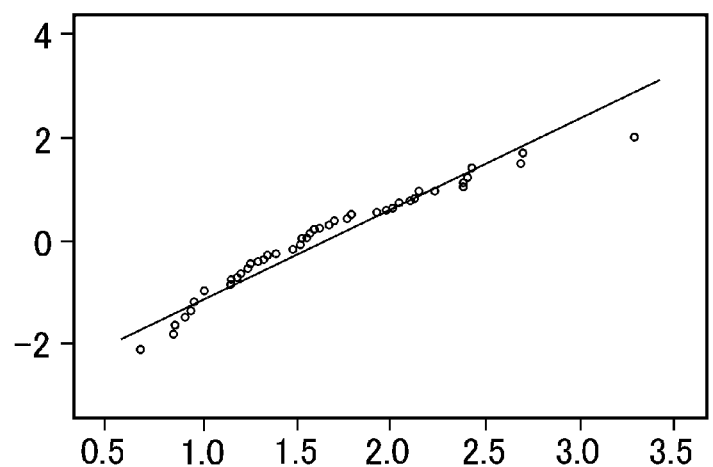
FIG.13

FIG.16

SOFTWARE, HEALTH CONDITION DETERMINATION APPARATUS, AND HEALTH CONDITION DETERMINATION METHOD

TECHNICAL FIELD

The present invention relates to a software, a health condition determination apparatus, and a health condition determination method. More specifically, the present invention relates to a software, a health condition determination apparatus, and a health condition determination method, each of which can understand different intra-subject variation for each subject with high accuracy by reflecting a vital sign considering an individual difference of the subject or daily condition of the subject, and can contribute to the health care of the subject or the provision of medical care suitable for each personality.

BACKGROUND ART

In recent years, "personalized medicine" has become increasingly important in medical fields. The term "personalized medicine" generally refers to "taking medicine according to individual personality" called "tailor-made medicine".

Medicine so far has been conducted focusing on disease, and a main purpose of medicine is to search for causes of the disease or to develop therapeutics therefor. It has been known that the state of disease varies from person to person and the application of the same therapy to the same disease is not necessarily correct.

However, in conventional medicine, an individual difference in therapeutic effect cannot be understood unless therapy and its effect are observed, so it is difficult to prescribe an optimal therapeutic regimen for each person.

Here, it is important to understand "biomarkers" which are different for individuals in the realization of individualized medicine. In general, a biomarker is an indicator for particular disease conditions or living organism conditions. In 1998, a working group of the American National Institutes of Health defined the term as "a characteristic that is objectively measured and evaluated as an indicator of normal biologic processes, pathogenic processes, or pharmacologic responses to a therapeutic intervention." In the past, a biomarker mainly means a physiological indicator, such as blood pressure or heart rate.

Meanwhile, there is a health care system for obtaining diagnosis value information of a subject by using a plurality of measurement apparatuses and then determining each diagnosis value to be normal or abnormal. A health care system disclosed in Patent Document has been suggested.

Here, the health care system disclosed in Patent Document 1 is configured to obtain diagnosis value information (vital signs) by using a body composition measurement apparatus connected to a user terminal, a blood pressure measurement apparatus, a urine glucose measurement apparatus, a blood glucose measurement apparatus, a body temperature measurement apparatus, and the like.

In addition, each diagnosis value information is recorded on database, and the determination whether or not the measured diagnosis value information is normal or abnormal is made based on a normal value of each user, for example, in consideration of an average value of three-day measurement information.

In addition, in a conventional determination of the health condition, including the health care system disclosed in Patent Document 1, an absolute value as a standard is prepared, and the ranking of health condition and the detection of abnormality are conducted by using the magnitude of a measurement value for the absolute value.

PRIOR ART DOCUMENT

Patent Document

Patent Document 1: Patent Publication No. 2011-227547

DETAILED DESCRIPTION OF THE INVENTION

Technical Problem

However, conventional structures for examining abnormality based on the measurement of vital information of a subject, including the health care system disclosed in patent document 1, are not an examination in consideration of intra-subject variation. Patent Document 1 merely discloses that the mean value of measurement information for only three days is used as a standard for a normal value, which is not an examination in consideration of intra-subject variation.

In addition, in a conventional art excluding Patent Document 1, when abnormality is determined from, for example, body temperature information, there are many cases in which the usual body temperature obtained by a reply from a subject is used as a standard value and then a body temperature value outside a range of 1.0° C. above or below the usual temperature is determined to be abnormal. It is considered that there is an individual difference in body temperature variation width even in the usual body temperature, and thus the usual body temperature cannot be an appropriate standard value.

That is, a person who should be determined to be normal despite a large body temperature displacement or a person who should be detected to be abnormal despite a small body temperature displacement cannot receive a proper determination. Such a configuration makes it difficult to evaluate a health condition with high accuracy.

Biomarkers suitable for the purposes, such as diagnosis, prognosis, pharmacodynamics, and monitoring, are indispensable in personalized medicine, which is expected to expand. The present inventors have conducted research mainly on biomarkers aimed at "disease development of the elderly" and "diagnosis" until now. Of these, the present inventors found the possibility in biomarkers used as "vital signs", such as body temperature, pulse rate, and blood pressure, which are the most basic information on human life, but not biomarkers for interpretation at the genetic level, which has been recently carried out.

The reason why these vital signs can be biomarkers is that there is a different "intra-subject variation" for each person in vital signs, such as a body temperature, a blood pressure, a pulse rate, or a respiration rate. That is, it is thought that the manner of vital sign change varies depending on the subject, and the proper understanding and interpretation of such a manner of change can develop techniques contributing to health care or diagnosis of the subject.

In addition, the present inventors have confirmed through research so far that basically, human vital signs are normally distributed in consideration of a distribution over a predetermined period. In addition, the normal distribution of a vital sign is a distribution including intra-subject variation inherent to each person.

However, there are papers or reports on "inter-subject variation" to confirm the standard deviation of many persons in association with vital signs, but there is no article dealing with "intra-subject variation" of the same subject.

In conventional medicine, there are many interpretations based on "inter-subject variation" whereby vital sign data of a plurality of different patients are integrated and the integration data of the plurality of patients are compared with vital sign data of a particular patient, but there is no interpretation based on the variations of vital signs of the same subject, that is, "intra-subject variation".

In conventional medicine, an interpretation based on "inter-subject variation" is frequently conducted, but an interpretation or diagnosis based on a normal distribution of "intra-subject variation" is rarely performed.

Under such circumstances, in vital signs, which are biomarkers useful in personalized medicine, and analysis thereof, the standard that sufficiently reflects the intra-subject variation of an individual subject is important, and the determination technique using the same is strongly requested.

In addition, the health condition determination technique using intra-subject variation has sufficient possibility to be utilized in the early detection of a condition in which a subject has an abnormal condition or to be utilized in self-care of condition or prevention in a stage before abnormal condition occurs, so called self-management.

The present invention has been made considering the above facts, and the present invention relates to a software, a health condition determination apparatus, and a health condition determination method, each of which can understand different intra-subject variation for each subject with high accuracy by reflecting a vital sign considering an individual difference of a subject or daily condition of the subject and can contribute to the provision of health care of a subject or medicine fitted for each personality.

Technical Solution

In accordance with an aspect of the present invention, there is provided A software for determining a health condition of a subject, based on vital information corresponding to a measured value of a vital sign, wherein the software allows an information processing device to function as a unit including: an information input unit configured to receive an input of the vital information measured from the same subject and measurement date and time information; an information recording unit configured to allow the input vital information and measurement date and time information to be recorded thereon; a standard calculation unit configured to calculate at least one selected from mean $\mu$ and standard deviation $\sigma$ of all or some of multiple pieces of vital information recorded; and a determination unit configured to determine whether or not the input predetermined vital information is an abnormal value, based on a predetermined numerical range set based on at least one selected from the mean $\mu$ and the standard deviation $\sigma$. In the present specification, the software refers to a program relating operation of a computer. In addition, the program refers to a sequence of ordered rows of instructions suitable for processing by the computer.

Here, the information input unit receives vital information measured from the same subject, and allows the input vital information to be recorded on the information recording unit, and thus the vital information of the same subject can be stored. The "same subject" stated herein indicates an object of determination for determining whether or not a measured vital sign value is an abnormal value.

The "subject" stated herein refers to a single living thing (human or animal). The present invention includes an aspect of recording vital information of the single same subject and an aspect of recording vital information of a plurality of same subjects for the same subject, in a single software. The same subject refers to the same person if for example, a human being.

The "vital information measured in the same subject" stated herein mean that a subject can be identified in an input stage by the information input unit. For example, a subject can be identified by varying a mode of input, such as an aspect in which a single subject inputs his or her own vital information or an aspect in which vital information is input on a particular personal input screen displayed when the information for a plurality of subjects is processed.

In addition, the information input unit receives an input of the vital information measured from the same subject and measurement date and time information, and the input vital information and the measurement date and time information are recorded on the information recording unit, so that the vital information of the same subject is accumulated together with the measurement date and time. That is, multiple pieces of vital information of the same subject can be processed in connection with the measurement date and time information. In addition, when compared with other vital information, a displacement situation or a displacement from the vital information to be compared. The "measurement date and time information" stated herein includes, when the vital information is input to the information input unit, an aspect in which an input person inputs the measurement date and time information or an aspect in which the input time of the vital information is automatically input.

In addition, the standard calculation unit calculates the mean $\mu$ of all or some of the recorded multiple pieces of vital information, thereby enabling the use of the information of the mean value of vital information in which the intra-subject variation of the same subject is reflected. The "mean $\mu$" stated herein refers to a value obtained by dividing "the sum of vital values" by "the number of vital data values". The "mean $\mu$ of the recorded multiple pieces of vital information" stated herein includes not only those being calculated from the whole data of recorded vital information, but also those calculated from some of the whole data. The vital information serving as the calculation basis of the mean $\mu$ may be calculated from continuous data, for example, data obtained by continuous daily measurement, as well as from data extracted with intervals of days. The "vital information serving as the calculation basis of the mean $\mu$" stated herein does not exclude vital values based on an abrupt displacement of vital value, as will be described later, or does not exclude vital values based on the content of health inquiry information.

In addition, the standard calculation unit calculates the standard deviation $\sigma$ of all or some of the recorded multiple pieces of vital information, thereby enabling the use of the information of the standard deviation of vital information in which the intra-subject variation of the same subject is reflected. The "standard deviation $\sigma$" stated herein refers to the "root mean square of deviation" of vital information for a predetermined period. In other words, the "deviation" is a value obtained by subtracting "mean value of vital values for a predetermined period" from "each vital value" of vital information for a predetermined period. The "standard deviation $\sigma$ of recorded multiple pieces of vital information" stated herein includes not only those being calculated from the whole data of recorded vital information, but also those calculated from some of the whole data. The vital information serving as the calculation basis of the standard deviation σ may be calculated from continuous data, for example, data obtained by continuous daily measurement, as well as from data extracted with intervals of days. The "vital information serving as the calculation basis of the standard deviation σ" stated herein does not exclude vital values based on an abrupt displacement of vital value, as will be described later, or does not exclude vital values based on the content of health inquiry information.

Furthermore, the standard calculation unit calculates at least one selected from the mean μ and the standard deviation σ of all or some of the recorded multiple pieces of vital information, and thus enables the calculation of any one of the mean μ and the standard deviation σ. Both of mean μ and standard deviation σ may also be calculated.

In addition, the determination unit determines whether or not the input predetermined vital information is an abnormal value based on a predetermined numerical range set based on at least one selected from the mean μ and the standard deviation σ, so that it can be determined, through a standard in which the intra-subject variation of the same subject is reflected, whether or not the vital information of the same subject is an abnormal value. That is, the predetermined numerical range serving as a determination standard is set by using the mean value or the standard deviation calculated from the vital information accumulated for the same subject, and thus the normality or abnormality can be determined by using the standard, which is unique to the same subject and in which the mean value of vital information or the dispersion from the mean value is reflected. The "input predetermined vital information" stated herein mean vital information serving as an object of determination. The "predetermined numerical range" stated herein includes both of a numerical value range set by including the input predetermined vital information, that is, predetermined vital information serving as an object of determination, and a numerical range set from the previous past vital information, not including the predetermined vital information as an object of determination. In addition, the "predetermined numerical range" includes, when a value serving as a standard, for example, the upper limit is set, an aspect in which a numerical value serving as an object of determination is determined to be abnormal if equal to or higher than the upper limit, and an aspect in which the numerical value is determined to be abnormal if higher than the upper limit. The input predetermined vital information may be recently input vital information. The input predetermined vital information may be one of previously input vital information or multiple pieces of vital information.

In a case in which the standard calculation unit calculates the mean μ and the standard deviation σ and calculates a normal distribution from the mean μ and the standard deviation σ, the vital information of the same subject for a certain period, for example, a probability density function with the same distribution, is easy to display through graphing, so that the deviation from the mean value or probability density can be easily confirmed.

When the standard calculation unit calculates the mean μ and the standard deviation σ from at least two pieces of vital information for a predetermined period recorded on the information recording unit, the mean μ and the standard deviation σ can be calculated from some data of the recorded multiple pieces of vital information rather than the whole data thereof.

When the standard calculation unit calculates the mean μ and the standard deviation σ from the vital information for 30 days or more recorded on the information recording unit, the mean μ and the standard deviation σ further reflecting the intra-subject variation of the same subject can be calculated. As a result, the accuracy of the standard for determination as to whether or not vital information is an abnormal value can be improved. The "vital information for 30 days or more" stated herein includes vital information for a total of 30 days or more including not only consecutive days but also days at intervals.

When the determination unit sets formulas (1) and (2) below, expressed by using mean μ, standard deviation σ, and n and m greater than 0, to the lower limit and the upper limit, respectively, and determines whether or not the input predetermined vital information is an abnormal value based on at least one of the lower limit and the upper limit, the determination standard can be set such that the numerical value distanced from the mean μ by nσ in a positive direction is the lower limit and the numerical value distanced from the mean μ by mσ is the upper limit.

$$\mu - n\sigma \qquad \text{formula (1)}$$

$$\mu + m\sigma \qquad \text{formula (2)}$$

That is, the value obtained by subtracting nσ from the mean μ is set to the lower limit value and the value obtained by adding mσ to the mean μ is set to the upper limit value, and based on at least one thereof, it can be determined whether or not the vital information is an abnormal value. In addition, the values of n and m may be a number greater than 0 as described above, and the values of n and m can be appropriately set in consideration of various conditions, such as strictness of determination standard, type of vital, past medical history of a subject, and the like. When the vital information is normally distributed, approximately 95% of vital information is distributed in the range of μ±2σ, which can be adopted as an example of the determination standard. The "at least one of the lower limit and the upper limit" includes an aspect in which only the lower limit or only the upper limit is set as a standard, as well as an aspect in which both the lower limit and the upper limit are adopted as a standard.

In addition, when the vital information includes value of a vital sign measured at least once in the morning and the afternoon on the same day, the highest and lowest values on that day can be checked, and thus the comparison of vital information can be possible in that day or between different days. For example, it can be determined that the vital value measured in the afternoon is an abnormal value if the displacement from the vital value measured in the morning is great and exceeds a predetermined displacement. Likewise, it can be determined that a measurement value is an abnormal value if the displacement of the highest value (or the lowest value) of the vital value between different dates exceeds a predetermined displacement. Since the vital information is recorded at least twice a day and the accumulation amount of data increases, mean μ and standard deviation σ further reflecting the intra-subject variation of the same subject can be calculated.

When the standard calculation unit calculates at least one of mean μ and standard deviation σ, in the multiple pieces of vital information recorded on the information recording unit, excluding the vital information, of which a displacement from the value of vital sign measured on the previous day exceeds a predetermined range, at least one of the mean value and the standard deviation of vital information reflecting a conformable condition of the same subject can be used. That is, the value on the day on which the vital information is abruptly changed is not included in the calculation basis of at least one of the mean value and the standard deviation, and thus the comfortable condition of the same subject is easy to understand. The "previous day" used in the expression of the value of vital information measured on the previous day mean vital information of "the day before" in consideration of the vital information obtained and recorded every day. For example, whether or not the value of the vital information six days ago, based on the day on which a determination of abnormality is made, is included in the calculation basis of the mean value depends on a displacement from the value of the vital information 7 days ago.

The "mean $\mu$" or "standard deviation $\sigma$" stated herein includes those calculated from the whole data of the vital information after the exclusion as well as those calculated from some of the whole data. The vital information serving as the calculation basis may be calculated from continuous data, for example, data obtained by continuous daily measurement, as well as from data extracted with intervals of days. The "at least one of the mean $\mu$ and the standard deviation $\sigma$" includes the calculation of only the mean $\mu$, the calculation of only standard deviation $\sigma$, and the calculation of both the mean $\mu$ and the standard deviation $\sigma$.

The determination unit determines whether or not the input predetermined vital information is an abnormal value based on a predetermined numerical range set based on at least one of the mean $\mu$ and the standard deviation $\sigma$, and thus can determine whether or not the vital information is an abnormal value according to the determination standard set based on at least one of the mean $\mu$ and the standard deviation $\sigma$ reflecting the comfortable condition of the same subject. The "predetermined numerical range" stated herein includes both of a numerical value range set by including the input predetermined vital information, that is, the vital information as an object of determination, and a numerical range set from the previous past vital information, not including the vital information as an object of determination. In addition, the "predetermined numerical range" includes, when a value serving as a standard, such as the upper limit, is set, an aspect in which a numerical value serving as an object of determination is determined to be abnormal if equal to or higher than the upper limit, and an aspect in which the numerical value is determined to be abnormal if higher than the upper limit. In addition, because of the "at least one of the mean $\mu$ and the standard deviation $\sigma$", the standard is set by including a combination of the mean $\mu$ calculated excluding the vital information and the standard deviation $\sigma$ calculated without excluding the vital information, a combination of the mean $\mu$ calculated without excluding the vital information and the standard deviation $\sigma$ calculated excluding the vital information, and a combination of the mean $\mu$ calculated excluding the vital information and the standard deviation $\sigma$ calculated excluding the vital information.

When there is a health inquiry information recording unit on which first health inquiry information, having determinations of normality or abnormality for respective items as one or more inquiry results regarding health condition of the same subject, is recorded together with date information of the inquiry day, the inquiry results confirmed by the same subject and the evaluation results considering the results as being normal or abnormal can be recorded together with the date information of the inquiry day. The inquiry content reflects information about the health condition on the day of determination or the previous day, and may include the content about the condition on that day, whether or not sufficient sleep was secured, or the like. The "a determination of normality or abnormality was made" in the health inquiry information mean the determination results determined by the subject's replies. More specifically, as for an inquiry of "How is your condition today?", a reply of "good" leads to a determination of "normal" and a reply of "bad" leads to a determination of "abnormal".

When the standard calculation unit calculates at least one of the mean $\mu$ and the standard deviation $\sigma$, based on the first health inquiry information recorded on the health inquiry information recording unit, in the multiple pieces of vital information recorded on the information recording unit, excluding the vital information measured on the day on which at least one abnormality is recorded in the content of the first health inquiry information, at least one of the mean value and the standard deviation of the vital information reflecting conformable condition of the same subject can be used. That is, the vital value on the day on which the abnormality is confirmed from the results of inquiry is not included in the calculation basis of at least one of the mean value and the standard deviation, and thus the comfortable condition of the same subject is easy to understand.

The "mean $\mu$" or "standard deviation $\sigma$" stated herein includes those calculated from the whole data of the vital information after the exclusion as well as those calculated from some of the whole data. The vital information serving as the calculation basis may be calculated from continuous data, for example, data obtained by continuous daily measurement, as well as from data extracted with intervals of days. The "at least one of the mean $\mu$ and the standard deviation $\sigma$" includes the calculation of only the mean $\mu$, the calculation of only standard deviation $\sigma$, and the calculation of both the mean $\mu$ and the standard deviation $\sigma$.

The determination unit determines whether or not the input predetermined vital information is an abnormal value, based on a predetermined numerical range set based on at least one of the mean $\mu$ and the standard deviation $\sigma$, and thus can determine whether or not the vital information is an abnormal value according to the determination standard set based on at least one of the mean $\mu$ and the standard deviation $\sigma$ reflecting the comfortable condition of the same subject. The "predetermined numerical range" stated herein includes both of a numerical value range set by including the input predetermined vital information, that is, the vital information as an object of determination, and a numerical range set from the previous past vital information, not including the vital information as an object of determination. In addition, the "predetermined numerical range" includes, when a value serving as a standard, such as the upper limit, is set, an aspect in which a numerical value serving as an object of determination is determined to be abnormal if equal to or higher than the upper limit, and an aspect in which the numerical value is determined to be abnormal if higher than the upper limit. In addition, because of the "at least one of the mean $\mu$ and the standard deviation $\sigma$", the standard is set by including a combination of the mean $\mu$ calculated excluding the vital information and the standard deviation $\sigma$ calculated without excluding the vital information, a combination of the mean $\mu$ calculated without excluding the vital information and the standard deviation $\sigma$ calculated excluding the vital information, and a combination of the mean $\mu$ calculated excluding the vital information and the standard deviation $\sigma$ calculated excluding the vital information.

When the standard calculation unit also calculates the recent vital mean value, which is the mean value of the values of the vital sign for the recent 7 days, and the control vital mean value, which is the mean value of the values of the vital sign for the last 30 days, from the vital information recorded on the information recording unit; the software also contains a software for allowing the information processing device to function as a second determination unit; and the second determination determines, as a value of condition deterioration tendency, when a difference between the recent vital mean value and the contrast vital mean value exceeds a predetermined range, the information of predicting the deterioration of health condition of the same subject based on a change in mean value of the vital information can be provided. That is, it is understood that, based on the instability of the vital mean value in the last one week and the last one month, a great change in the vital mean value itself indicates a large change in health condition of the same subject as an object, and this is used as a prediction information causing abnormality. In addition, the "recent" stated herein may adopt both of an aspect of including vital information as an object of determination and an aspect of not including the vital information.

When the information input unit determines the input predetermined vital information to be an abnormal value and then receives an input of re-measurement vital information of the same subject and the measurement date and time information, and the information recording unit records the re-measurement vital information and the measurement date and time information therein, the vital information of the same subject through re-measurement, in addition to the vital information serving as the determination basis, can be recorded. For example, in the case where the value of vital information serving as the determination basis is an erroneous value for a certain reason and the measurement value is determined to be an abnormal value, the input and recording of the vital information for again investigating whether or not the determination result is accurate are performed.

When the software also contains a software for allowing the information processing device to function as a third determination unit and the third determination unit determines whether or not the re-measurement vital information is an abnormal value, the determination of the re-measured vital information can be made. That is, for example, in the case where the value of vital information serving as the basis of the first determination, an abnormal value, is an erroneous value for a certain reason, the normality or abnormality can be again determined. Furthermore, in this case, the mean value and the standard deviation used in the next determination and the determination standard set based thereon may be created using the re-measurement vital information.

When target measurement time information, which is the information of the target time for performing vital measurement, is stored in the information recording unit, timing information can be recorded for the same subject to measure vital information. In addition, a time difference between the actual measurement date and time of the vital information and the target measurement time information can be calculated.

When the standard calculation unit calculates at least one of the mean $\mu$ and the standard deviation $\sigma$, in the multiple pieces of vital information recorded on the information recording unit, excluding the vital information of which a time difference from the target measurement time information exceeds a predetermined range, the value of the vital information measured at the time deviating from the uniform measurement target time is not included in the calculation basis of at least one of the mean value and the standard deviation, so that the mean value or the standard deviation can be calculated from only the values of the vital information measured at a certain determined time zone.

The "mean $\mu$" or "standard deviation $\sigma$" stated herein includes those calculated from the whole data of the vital information after the exclusion as well as those calculated from some of the whole data. The vital information serving as the calculation basis may be calculated from continuous data, for example, data obtained by continuous daily measurement, as well as from data extracted with intervals of days. The "at least one of the mean $\mu$ and the standard deviation $\sigma$" includes the calculation of only the mean $\mu$, the calculation of only standard deviation $\sigma$, and the calculation of both the mean $\mu$ and the standard deviation $\sigma$.

The determination unit determines whether or not the input predetermined vital information is an abnormal value, based on the predetermined numerical range set based on at least one of the mean $\mu$ and the standard deviation $\sigma$, and thus can determine the normality or abnormality of the vital information by using the standard in which the intra-subject variation is more accurately reflected. That is, since the mean value or the standard deviation is calculated from the vital information with a small deviation in the measurement time and the determination can be performed on the calculated mean value or standard deviation, the vital information of the same subject, which varies with the time of one day, can be easily reflected. The "predetermined numerical range" stated herein includes both of a numerical value range set by including the input predetermined vital information, that is, the vital information as an object of determination, and a numerical range set from the previous past vital information, not including the vital information as an object of determination. In addition, the "predetermined numerical range" includes, when a value serving as a standard, such as the upper limit, is set, an aspect in which a numerical value serving as an object of determination is determined to be abnormal if equal to or higher than the upper limit, and an aspect in which the numerical value is determined to be abnormal if higher than the upper limit. In addition, because of the "at least one of the mean $\mu$ and the standard deviation $\sigma$", the standard is set by including a combination of the mean $\mu$ calculated excluding the vital information and the standard deviation $\sigma$ calculated without excluding the vital information, a combination of the mean $\mu$ calculated without excluding the vital information and the standard deviation $\sigma$ calculated excluding the vital information, and a combination of the mean $\mu$ calculated excluding the vital information and the standard deviation $\sigma$ calculated excluding the vital information.

When the types of vital signs include at least one selected from body temperature, pulse rate, systolic blood pressure, diastolic blood pressure, and respiration rate, it can be determined whether the vital information is a normal value or an abnormal value based on the values of at least one vital sign of body temperature, pulse rate, systolic blood pressure, diastolic blood pressure, and respiration rate.

When the standard calculation unit calculates at least one of the mean $\mu$ and the standard deviation $\sigma$ by including predetermined vital information recorded on the information recording unit, containing the values of the vital sign of the same subject and the measurement date and time information, the determination standard is calculated after the vital information as an object of determination is included. As a result, the determination can be performed in a form of containing vital information reflecting the condition of a subject on the day of determination.

When individual identification information capable of identify subjects individually can be recorded in connection with the vital information in the information recording unit, each piece of vital information can be identified and processed for each subject. That is, for example, a single software manages vital information of a plurality of subjects, and thus it is possible to determine vital information of a plurality of subjects.

When the vital sign is measured from at least one of humans and animals, a subject of determination can be set to a human being or an animal. The "animal" stated herein is not particularly delimited, and thus any animal can be an object of determination of abnormality as long as a value of a vital sign of the animal can be measured.

When the vital information is configured to include standard vital information containing values of a vital sign measured before a predetermined measurement start time point and the measurement date and time information, the values of vital sign of a subject measured at a particular timing and the measurement date and time information are input and recorded. The "before the predetermined measurement start time point" stated herein refers to the time point before the start of work if the subject is a worker who performs work at a certain work site. A person who lives an usual life, even not the worker who performs work, for example, an elderly person living alone, a resident in a nursing facility, a housewife, a child, or the like may be the subject, and a predetermined time in the morning may be set as a time before the predetermined measurement start time point.

When the vital information is configured to include monitoring vital information containing values of a vital sign measured multiple times during a predetermined time from the predetermined measurement start time point and measurement date and time information, the values of vital sign measured at multiple timings during a predetermined time from the predetermined measurement start time point and the measurement date and time information are input and recorded. The "during a predetermined time from the predetermined measurement start time point" stated herein includes, in a case of a worker who performs work, from the start of work to the end of work in one day, during a predetermined interval, such as in the morning or afternoon, an activity time in which a particular work is performed, or the like. In addition, the above statement includes, in a case of a person who lives a usual life, during from the start of activity to bedtime, during a predetermined time in the room, during certain activity, or the like. The "measurement multiple times" includes, for example, measurements performed at regular intervals, vital measurements at each of set multiple time points, or the like.

When the vital information is configured of: standard vital information containing values of a vital sign measured before a predetermined measurement start time point and measurement date and time information; and monitoring vital information containing values of a vital sign measured multiple times during a predetermined time from a predetermined measurement start time point and measurement date and time information, the vital information divided before and after the predetermined measurement start time point can be processed. That is, for example, a person who performs work can process standard vital information before work and monitoring vital information during work by setting the work start time point to a predetermined measurement start time point.

When the standard calculation unit calculates at least one of the mean $\mu$ and the standard deviation $\sigma$ of vital information from at least one of the standard vital information and the monitoring vital information, at least one of the mean value and the standard deviation of vital information based on at least one of the standard vital information and the monitoring vital information can be used. That is, for example, if the subject is a person who performs work, the mean value and the standard deviation of the vital information in which the intra-subject variation reflecting a comfortable condition before work or the condition during work is reflected can be used.

The "mean $\mu$" or "standard deviation $\sigma$" stated herein includes those calculated from the whole data of the recorded multiple pieces of vital information as well as those calculated from some of the whole data. The vital information serving as the calculation basis may be calculated from continuous data, for example, data obtained by continuous daily measurement, as well as from data extracted with intervals of days. Since the "mean $\mu$ and standard deviation" are values calculated from "at least one of standard vital information and monitoring vital information", the calculation includes the calculation from only standard vital information, the calculation from only monitoring vital information, and the calculation from both of standard vital information and monitoring vital information.

The determination unit determines whether or not the input vital information is an abnormal value based on a predetermined numerical range set based on the mean $\mu$ and the standard deviation $\sigma$, and thus can determine whether or not the vital information is not an abnormal value on according to the determination standard set based on at least one of the mean $\mu$ and the standard deviation $\sigma$ in which the condition of the same subject before and after the predetermined measurement start time point is reflected. The "predetermined numerical range" stated herein includes both of a numerical value range set by including the input predetermined vital information, that is, the vital information as an object of determination, and a numerical range set from the previous past vital information, not including the vital information as an object of determination. In addition, the "predetermined numerical range" includes, when a value serving as a standard, such as the upper limit, is set, an aspect in which a numerical value serving as an object of determination is determined to be abnormal if equal to or higher than the upper limit, and an aspect in which the numerical value is determined to be abnormal if higher than the upper limit. The "object of determination about abnormality" stated herein is both standard vital information and monitoring vital information.

When the standard calculation unit calculates the mean $\mu$ and the standard deviation $\sigma$ of vital information from standard vital information and monitoring vital information, the mean $\mu$ and the standard deviation $\sigma$ can be calculated by reflecting the variation of the values of a vital sign in both of the standard vital information and monitoring vital information.

When the determination unit sets formulas (1) and (2) below, expressed by using the mean $\mu$, standard deviation $\sigma$, and n and m greater than 0, to the lower limit and the upper limit, respectively, and determines whether or not the input predetermined vital information is an abnormal value based on at least one of the lower limit and the upper limit, the determination standard can be set such that the numerical value distanced from the mean $\mu$ by $n\sigma$ in a positive direction is the lower limit and the numerical value distanced from the mean $\mu$ by $m\sigma$ is the upper limit.

$$\mu - n\sigma \qquad \text{Formula (1)}$$

$$\mu + m\sigma \qquad \text{Formula (2)}$$

That is, the value obtained by subtracting $n\sigma$ from the mean $\mu$ is set to the lower limit value and the value obtained by adding $m\sigma$ to the mean $\mu$ is set to the upper limit value, and based on at least one thereof, it can be determined whether or not the vital information is an abnormal value. In addition, the values of n and m may be a number greater than 0 as described above, and the values of n and m can be appropriately set in consideration of various conditions, such as strictness of determination standard, type of vital, past medical history of a subject, and the like. The "at least one of the lower limit and the upper limit" includes an aspect in which only the lower limit or only the upper limit is set as a standard, as well as an aspect in which both the lower limit and the upper limit are adopted as a standard.

When there is a health inquiry information recording unit on which second health inquiry information, having determinations of normality or abnormality for respective items as one or more inquiry results regarding health condition of the same subject, is recorded together with date information of the inquiry day, the inquiry results confirmed by the same subject and the evaluation results considering the results as being normal or abnormal can be recorded together with the date information of the inquiry day. The inquiry content reflects the information about the health condition of a subject on the day of determination or the previous day, and may include, for example, the content about the condition on that day, the sleeping time during the night before, whether or not sufficient sleep was secured, whether or not the subject dank alcohol on the previous day, the degree of inebriation on that day, and the like. The "a determination of normality or abnormality was made" in the health inquiry information mean the determination results determined by the subject's replies. More specifically, as for an inquiry of "How is your condition today?", a reply of "good" leads to a determination of "normal" and a reply of "bad" leads to a determination of "abnormal".

When the standard calculation unit calculates at least one of the mean $\mu$ and the standard deviation $\sigma$, based on the second health inquiry information recorded on the health inquiry information recording unit, in the multiple pieces of vital information recorded on the information recording unit, excluding the vital information measured on the day on which at least one abnormality is recorded in the content of the second health inquiry information, at least one of the mean value and the standard deviation of the vital information reflecting conformable condition of the same subject can be used. That is, the vital value on the day on which the abnormality is confirmed from the results of inquiry is not included in the calculation basis of at least one of the mean value and the standard deviation, and thus the comfortable condition of the same subject is easy to understand.

The "mean $\mu$" or "standard deviation $\sigma$" stated herein includes those calculated from the whole data of the vital information after the exclusion as well as those calculated from some of the whole data. The vital information serving as the calculation basis may be calculated from continuous data, for example, data obtained by continuous daily measurement, as well as from data extracted with intervals of days. The "at least one of the mean $\mu$ and the standard deviation $\sigma$" includes the calculation of only the mean $\mu$, the calculation of only standard deviation $\sigma$, and the calculation of both the mean $\mu$ and the standard deviation $\sigma$.

The determination unit determines whether or not the input predetermined vital information is an abnormal value, based on a predetermined numerical range set based on at least one of the mean $\mu$ and the standard deviation $\sigma$, and thus can determine whether or not the vital information is an abnormal value according to the determination standard set based on at least one of the mean $\mu$ and the standard deviation $\sigma$ reflecting the condition of the same subject before and after a predetermined measurement start time point and the comfortable condition of the same subject. The "predetermined numerical range" stated herein includes both of a numerical value range set by including the input predetermined vital information, that is, the vital information as an object of determination, and a numerical range set from the previous past vital information, not including the vital information as an object of determination. In addition, the "predetermined numerical range" includes, when a value serving as a standard, such as, the upper limit, is set, an aspect in which a numerical value serving as an object of determination is determined to be abnormal if equal to or higher than the upper limit, and an aspect in which the numerical value is determined to be abnormal if higher than the upper limit. In addition, because of the "at least one of the mean $\mu$ and the standard deviation $\sigma$", the standard is set by including a combination of the mean $\mu$ calculated excluding the vital information and the standard deviation $\sigma$ calculated without excluding the vital information, a combination of the mean $\mu$ calculated without excluding the vital information and the standard deviation $\sigma$ calculated excluding the vital information, and a combination of the mean $\mu$ calculated excluding the vital information and the standard deviation $\sigma$ calculated excluding the vital information.

When the standard calculation unit calculates at least one of the mean $\mu$ and the standard deviation $\sigma$, in the multiple pieces of vital information recorded on the information recording unit, excluding the vital information, of which a displacement from the vital sign value measured on the previous day or before one timing exceeds a predetermined range, at least one of the mean value and the standard deviation of vital information reflecting the condition of the same subject before and after a predetermined measurement start time point and a conformable condition of the same subject can be used. That is, the value at the timing at which the vital information abruptly deteriorates is not included in the calculation basis of at least one of the mean value and the standard deviation, and thus the comfortable condition of the same subject is easy to understand. The "value of vital information measured on the previous day or before one timing" stated herein mean, for example, "standard vital information on the previous day" when the measurement timing of the standard vital information is set to once a day or "monitoring vital information measured before one timing" in the monitoring vital information measured multiple times on the same day. The above statement may include "monitoring vital information measured at the same time zone on the previous day".

The "mean $\mu$" or "standard deviation $\sigma$" stated herein includes those calculated from the whole data of the vital information after the exclusion as well as those calculated from some of the whole data. The vital information serving as the calculation basis may be calculated from continuous data, for example, data obtained by continuous daily measurement, as well as from data extracted with intervals of days. The "at least one of the mean $\mu$ and the standard deviation $\sigma$" includes the calculation of only the mean $\mu$, the calculation of only standard deviation $\sigma$, and the calculation of both the mean $\mu$ and the standard deviation $\sigma$.

The determination unit determines whether or not the input predetermined vital information is an abnormal value, based on a predetermined numerical range set based on at least one of the mean $\mu$ and the standard deviation $\sigma$, and thus can determine whether or not the vital information is an abnormal value according to the determination standard set based on at least one of the mean μ and the standard deviation σ reflecting the condition of the same subject before and after a predetermined measurement start time point and the comfortable condition of the same subject. The "predetermined numerical range" stated herein includes both of a numerical value range set by including the input predetermined vital information, that is, the vital information as an object of determination, and a numerical range set from the previous past vital information, not including the vital information as an object of determination. In addition, the "predetermined numerical range" includes, when a value serving as a standard, such as the upper limit, is set, an aspect in which a numerical value serving as an object of determination is determined to be abnormal if equal to or higher than the upper limit, and an aspect in which the numerical value is determined to be abnormal if higher than the upper limit. In addition, because of the "at least one of the mean μ and the standard deviation σ", the standard is set by including a combination of the mean μ calculated excluding the vital information and the standard deviation σ calculated without excluding the vital information, a combination of the mean μ calculated without excluding the vital information and the standard deviation σ calculated excluding the vital information, and a combination of the mean μ calculated excluding the vital information and the standard deviation σ calculated excluding the vital information.

In accordance with another aspect of the present invention, there is provided a software for determining a health condition of a subject, based on vital information including: standard vital information containing a value of a vital sign measured before a predetermined measurement start time point and measurement date and time information thereof; and monitoring vital information containing values of the vital sign measured multiple times during a predetermined time from the predetermined measurement start time point and measurement date and time information thereof, wherein the software allows an information processing device to function as a unit including: an information input unit configured to receive an input of the vital information measured from the same subject; an information recording unit configured to allow the input vital information to be recorded thereon; a health inquiry information recording unit configured to allow third health inquiry information to be recorded together with date information of inquiry days thereon, the third health inquiry information having determinations of normality or abnormality for respective items as a plurality of inquiry results regarding the health condition of the same subject; a standard mean value calculation unit configured to calculate the mean μ of all or some of the vital information, based on the third health inquiry information recorded on the health inquiry information recording unit, in the multiple pieces of vital information recorded on the information recording unit, excluding vital information measured on a day on which at least one determination of abnormality is recorded in the content of the third health inquiry information; and a determination unit configured to determine whether or not the vital information is an abnormal value, by comparing, with a predetermined numerical value, a difference between the mean value μ and the value of the vital sign of the input predetermined vital information or a difference between the mean value μ and the mean μ at the time of measurement on the previous day or before one timing.

Here, the vital information includes: standard vital information containing a value of a vital sign measured before a predetermined measurement start time point and measurement date and time information, so that a value of the vital sign measured at a particular timing and measurement date and time information thereof are input and recorded. The "before a predetermined measurement start time point" stated herein refers to the time point of work start, if the subject is a worker who performs work at a certain work site. For example, an elderly person living alone, a resident in a nursing facility, a housewife, a child, or the like, besides a worker who performs work, may be the subject, and a predetermined time in the morning may be set as a time before the predetermined measurement start time point.

The vital information includes monitoring vital information containing values of a vital sign measured multiple times during a predetermined time from the predetermined measurement start time point and measurement date and time information thereof, so that the values of the vital sign measured at multiple timings during the predetermined time from the predetermined measurement start time point and the measurement date and time information thereof are input and recorded. The "during a predetermined time from the predetermined measurement start time point" stated herein includes, for example, in a case of a worker who performs work, during from the start of work to the end of work in one day, during a predetermined interval, such as in the morning or afternoon, during an activity time while a particular work is performed, or the like. In addition, the above statement includes, in a case of a person who lives a usual life, during from the start of activity to bedtime, during a predetermined time in the room, during certain activity, or the like. The "multiple times of measurement" includes, for example, measurements performed at regular intervals, vital measurements at each of set multiple time points, or the like.

The vital information includes: standard vital information containing a value of a vital sign measured before a predetermined measurement start time point and measurement date and time information thereof; and monitoring vital information containing values of a vital sign measured multiple times during a predetermined time from a predetermined measurement start time point and measurement date and time information thereof, so that the vital information divided before and after the predetermined measurement start time point can be processed. That is, for example, a person who performs work can process standard vital information before work and monitoring vital information during work by setting the work start time point to a predetermined measurement start time point.

There is a health inquiry information recording unit on which third health inquiry information, having determinations of normality or abnormality for respective items as one or more inquiry results regarding health condition of the same subject, is recorded together with date information of inquiry days, so that the inquiry results confirmed by the same subject and the evaluation results considering the results as being normal or abnormal can be recorded together with the date information of the inquiry day. The inquiry content reflects the information about the health condition of a subject on the day of determination or the previous day, and may include, for example, the content about the condition on that day, the sleeping time during the night before, whether or not sufficient sleep was secured, whether or not the subject drank on the previous day, the degree of inebriation on that day, and the like. The "a determination of normality or abnormality was made" in the health inquiry information mean the determination results determined by the subject's replies. More specifically, as for an inquiry of "How is your condition today?", a reply of "good" leads to a determination of "normal" and a reply of "bad" leads to a determination of "abnormal".

In addition, the standard mean value calculation unit calculates the mean µ of all or some of the vital information, based on the third health inquiry information recorded on the health inquiry information recording unit, in the multiple pieces of vital information recorded on the information recording unit, excluding vital information measured on a day on which at least one abnormality is recorded in the content of the third health inquiry information, so that the mean value of the vital information reflecting a comfortable condition of the same subject can be used. That is, the vital value on the day on which the abnormality is confirmed from the results of inquiry is not included in the calculation basis of the mean value, and thus the comfortable condition of the same subject is easy to understand.

The "mean µ" stated herein includes one calculated from the whole data of the vital information after the exclusion as well as one calculated from some of the whole data. The vital information serving as the calculation basis may be calculated from continuous data, for example, data obtained by continuous daily measurement, as well as from data extracted with intervals of days. In addition, the "mean µ" includes the calculation from only the standard vital information, the calculation from only the monitoring vital information, and the calculation from both of the standard vital information and the monitoring vital information.

The determination unit determines whether or not the vital information is an abnormal value, by comparing, with a predetermined numerical value, a difference between the mean value µ and a value of a vital sign of the input predetermined vital information or a difference between the mean value µ and the mean µ at the time of measurement on the previous day or before one timing, and thus can determine whether or not the vital information is an abnormal value, by using the mean value of the vital information in which the condition of the same subject before and after the predetermined measurement start time point and the comfortable condition of the same subject are reflected. In addition, the "predetermined numerical value" stated herein includes, when a value serving as a standard, for example, the upper limit is set, an aspect in which a numerical value serving as an object of determination is determined to be abnormal if equal to or higher than the upper limit, and an aspect in which the numerical value is determined to be abnormal if higher than the upper limit. The object of determination about abnormality herein is both standard vital information and monitoring vital information. The "predetermined numerical value" stated herein is a value that can be properly set according to the kind of vital sign.

When the standard calculation unit calculates the mean µ, in the multiple pieces of vital information recorded on the information recording unit, excluding the vital information, of which a displacement from the vital sign value measured on the previous day or before one timing exceeds a predetermined range, the mean value of vital information reflecting the condition of the same subject before and after a predetermined measurement start time point and a conformable condition of the same subject can be used. That is, the value on the day on which the vital information is abruptly changed is not included in the calculation basis of the mean value, and thus the comfortable condition of the same subject is easy to determine. The "value of vital information measured on the previous day or before one timing" stated herein mean, for example, "standard vital information on the previous day" when the measurement timing of the standard vital information is set to once a day or "monitoring vital information measured before one timing" in the monitoring vital information measured multiple times on the same day. The above statement may include "monitoring vital information measured at the same time zone on the previous day".

The "mean µ" stated herein includes one calculated from the whole data of the vital information after the exclusion as well as one calculated from some of the whole data. The vital information serving as the calculation basis may be calculated from continuous data, for example, data obtained by continuous daily measurement, as well as from data extracted with intervals of days. In addition, the "mean µ" includes the calculation from only the standard vital information, the calculation from only the monitoring vital information, and the calculation from both of the standard vital information and the monitoring vital information.

In addition, the determination unit determines whether or not the input vital information is an abnormal value based on the mean µ, and thus can determine whether or not the vital information is an abnormal value, by using the mean value of the vital information in which the condition of the same subject before and after the predetermined measurement start time point and the comfortable condition of the same subject. The determination herein includes, when a value serving as a standard, such as the upper limit, is set, both of an aspect in which a numerical value serving as an object of determination is determined to be abnormal if equal to or higher than the upper limit, and an aspect in which the numerical value is determined to be abnormal if higher than the upper limit. The object of determination about abnormality herein is both standard vital information and monitoring vital information.

In accordance with another aspect of the present invention, there is provided a software for determining a health condition of a subject, based on vital information corresponding to a measured value of a vital sign, wherein the software allows an information processing device to function as a unit including: an information input unit configured to receive an input of the vital information measured from the same subject and measurement date and time information thereof; an information recording unit configured to allow the input vital information and measurement date and time information to be recorded thereon; a standard mean value calculation unit configured to calculate the mean µ of all or some of the vital information, in the multiple pieces of vital information recorded on the information recording unit, excluding vital information, of which a displacement from a value of the vital sign measured on the previous day or before one timing exceeds a predetermined range; and a determination unit configured to determine whether or not the input vital information is an abnormal value, by comparing, with a predetermined numerical value, a difference between the mean µ and a value of a vital sign of the input vital information or a difference between the mean µ and the mean µ at the time of measurement on the previous day.

Here, the standard calculation unit calculates the mean µ of all or some of the vital information, in the multiple pieces of vital information recorded on the information recording unit, excluding the vital information, of which a displacement from the vital sign value measured on the previous day or before one timing exceeds a predetermined range, so that the mean value of vital information reflecting the condition of the same subject before and after the predetermined measurement start time point and the conformable condition of the same subject can be used. That is, the value at the timing at which the vital information abruptly deteriorates is not included in the calculation basis of the mean value, and thus the comfortable condition of the same subject is easy to understand. The "value of vital information measured on the previous day or before one timing" stated herein mean, for example, "standard vital information on the previous day" when the measurement timing of the standard vital information is set to once a day or "monitoring vital information measured before one timing" in the monitoring vital information measured multiple times on the same day. The above statement may include "monitoring vital information measured at the same time zone on the previous day".

The "mean $\mu$" stated herein includes one calculated from the whole data of the vital information after the exclusion as well as one calculated from some of the whole data. The vital information serving as the calculation basis may be calculated from continuous data, for example, data obtained by continuous daily measurement, as well as from data extracted with intervals of days. In addition, the "mean $\mu$" includes the calculation from only the standard vital information, the calculation from only the monitoring vital information, and the calculation from both of the standard vital information and the monitoring vital information.

The determination unit determines whether or not the vital information is an abnormal value, by comparing, with a predetermined numerical value, a difference between the mean value $\mu$ and a value of a vital sign of the input predetermined vital information or a difference between the mean value $\mu$ and the mean $\mu$ at the time of measurement on the previous day, and thus can determine whether or not the vital information is an abnormal value, by using the mean value of the vital information reflecting the condition of the same subject before and after the predetermined measurement start time point and the comfortable condition of the same subject. The "predetermined numerical value" stated herein includes, when a value serving as a standard, such as the upper limit, is set, an aspect in which a numerical value serving as an object of determination is determined to be abnormal if equal to or higher than the upper limit, and an aspect in which the numerical value is determined to be abnormal if higher than the upper limit. The object of determination about abnormality herein is both standard vital information and monitoring vital information. The "predetermined numerical value" stated herein is a value that can be properly set according to the kind of vital sign.

When there is a health inquiry information recording unit on which fourth health inquiry information, having determinations of normality or abnormality for respective items as one or more inquiry results regarding health condition of the same subject, is recorded together with date information of the inquiry day, the inquiry results confirmed by the same subject and the evaluation results considering the results as being normal or abnormal can be recorded together with the information of the inquiry day. The inquiry content reflects the information about the health condition of the subject on the day of determination or the previous day, and may include, for example, the content about the condition on that day, the sleeping time during the night before, whether or not sufficient sleep was secured, whether or not the subject drank on the previous day, the degree of inebriation on that day, and the like. The "a determination of normality or abnormality was made" in the health inquiry information herein mean the determination results determined by the subject's replies. More specifically, as for an inquiry of "How is your condition today?", a reply of "good" leads to a determination of "normal" and a reply of "bad" leads to a determination of "abnormal".

In addition, the standard mean value calculation unit calculates the mean $\mu$, based on the fourth health inquiry information recorded on the health inquiry information recording unit, in the multiple pieces of vital information recorded on the information recording unit, excluding the vital information measured on a day on which at least one abnormality is recorded in the content of the third health inquiry information, so that the mean value of the vital information reflecting a comfortable condition of the same subject can be used. That is, the vital value on the day on which the abnormality is confirmed from the results of inquiry is not included in the calculation basis of the mean value, and thus the comfortable condition of the same subject is easy to understand.

The "mean $\mu$" stated herein includes one calculated from the whole data of the vital information after the exclusion as well as one calculated from some of the whole data. The vital information serving as the calculation basis may be calculated from continuous data, for example, data obtained by continuous daily measurement, as well as from data extracted with intervals of days. In addition, the "mean $\mu$" includes the calculation from only the standard vital information, the calculation from only the monitoring vital information, and the calculation from both of the standard vital information and the monitoring vital information.

In addition, the determination unit determines whether or not the input vital information is an abnormal value based on the mean $\mu$, and thus can determine whether or not the vital information is an abnormal value, by using the mean value of the vital information in which the condition of the same subject before and after the predetermined measurement start time point and the comfortable condition of the same subject. The determination herein includes, when a value serving as a standard, such as the upper limit, is set, both of an aspect in which a numerical value serving as an object of determination is determined to be abnormal if equal to or higher than the upper limit, and an aspect in which the numerical value is determined to be abnormal if higher than the upper limit. The object of determination about abnormality herein is both standard vital information and monitoring vital information. The "predetermined numerical value" stated herein is a value that can be properly set according to the kind of vital sign.

In accordance with another aspect of the present invention, there is provided a health condition determination apparatus for determining a health condition of a subject, based on vital information corresponding to a measured value of a vital sign, the health condition determination apparatus including: an information input unit configured to receive an input of the vital information measured from the same subject and measurement date and time information thereof; an information recording unit configured to allow the input vital information and measurement date and time information thereof to be recorded thereon; a standard calculation unit configured to calculate at least one selected from mean $\mu$ and standard deviation $\sigma$ of all or some of multiple pieces of the recorded vital information; a determination unit configured to determine whether or not the input vital information is an abnormal value, based on a predetermined numerical value set based on at least one selected from the mean $\mu$ and the standard deviation $\sigma$; and a display unit configured to allow a determination result by the determination unit to be displayable thereon.

Here, the determination unit determines whether or not the input vital information is an abnormal value based on a predetermined numerical range set based on at least one selected from the mean $\mu$ and the standard deviation $\sigma$, and thus can determine whether or not the vital information of the same subject is an abnormal value by using a standard reflecting the intra-subject variation of the same subject. That is, the predetermined numerical range serving as a determination standard is set by using the mean value and the standard deviation calculated from the vital information accumulated for the same person, and thus the normality or abnormality can be determined by using the standard, which is unique to the person and which reflects the mean value of vital information or the dispersion from the mean value.

The determination results by the determination unit can be displayed and confirmed on the display unit.

When the display information creation unit creates a body temperature table based on the vital information recorded on the information recording unit, the vital trend of the same subject can be summarized on the body temperature table. The body temperature table means that the vital information for the same subject and the date information about the day of measurement of the vital information are displayed in a graph.

When the display information creation unit creates a normal distribution curve obtained by grappling the possibility density function of the normal distribution based on the normal distribution calculated from the vital information for a predetermined period, the distribution of the vital information of the same subject for a predetermined period can be summarized through the normal distribution curve.

When the display unit can display the body temperature table and the normal distribution curve created by the display information creation unit, the body temperature or the normal distribution curve can be visually confirmed, and the characteristics of the change in the vital information of the same subject reflecting the intra-subject variation is easy to understand. Furthermore, the body temperature table and the normal distribution curve can be easily used in more detailed analysis or an application to medical diagnosis.

In accordance with an aspect of the present invention, there is provided a health condition determination method for determining a health condition of a subject, based on vital information corresponding to a measured value of a vital sign, the method including: a standard calculating step for calculating at least one selected from mean $\mu$ and standard deviation $\sigma$ of vital information during a predetermined number of days or more, in the vital information measured from the same subject; and a determining step for determining whether or not the input predetermined vital information is an abnormal value, based on a predetermined numerical range set based on at least one selected from the mean $\mu$ and the standard deviation $\sigma$.

In the standard calculation step, at least one selected from the mean $\mu$ and the standard deviation $\sigma$ of the vital information for a predetermined number of days or more, in the vital information measured from the same subject, is calculated, so that the information of the mean value of the vital information reflecting the intra-subject variation of the same subject can be used. The "mean $\mu$" stated herein includes one calculated from the whole data of the vital information measured from the same subject as well as one calculated from some of the whole data. The vital information serving as the calculation basis of the mean $\mu$ may be calculated from continuous data, for example, data obtained by continuous daily measurement, as well as from data extracted with intervals of days. The "vital information serving as the calculation basis of the mean $\mu$" stated herein does not exclude a vital value based on an abrupt displacement of vital value, or does not exclude a vital value based on the content of health inquiry information.

Also, in the standard calculation step, at least one selected from the mean $\mu$ and the standard deviation $\sigma$ of the vital information for a predetermined number of days or more, in the vital information measured from the same subject, is calculated, so that the information of the standard deviation of the vital information reflecting the intra-subject variation of the same subject can be used. The "standard deviation $\sigma$" stated herein refers to the "root mean square of deviation" of vital information for a predetermined period of time. In other words, the "deviation" is a value obtained by subtracting "mean value of vital values for a predetermined period of time" from "each vital value" of vital information for a predetermined period of time. The "standard deviation $\sigma$" stated herein includes one calculated from the whole data of the vital information measured from the same subject as well as one calculated from some of the whole data. The vital information as the calculation basis of the standard deviation mean $\sigma$ may be calculated from continuous data, for example, data obtained by continuous daily measurement, as well as from data extracted with intervals of days. The "vital information serving as the calculation basis of the standard deviation $\sigma$" stated herein does not exclude a vital value based on an abrupt displacement of vital value, or does not exclude a vital value based on the content of health inquiry information.

Also, in the determination step, it is determined whether or not the input vital information is an abnormal value based on a predetermined numerical range set based on at least one selected from the mean $\mu$ and the standard deviation $\sigma$, and thus it can be determined whether or not the vital information of the same subject is an abnormal value, by using a standard reflecting the intra-subject variation of the same subject. That is, the predetermined numerical range serving as a determination standard is set by using the mean value and the standard deviation calculated from the vital information accumulated for the same person, and thus the normality or abnormality can be determined by using the standard, which is unique to the person and which reflects the mean value of vital information or the distribution from the mean value. The "input predetermined vital information" stated herein mean vital information serving as an object of determination. The "predetermined numerical range" stated herein includes both of a numerical value range set by including the input predetermined vital information, that is, the vital information as an object of determination, and a numerical range set from the previous past vital information, not including the vital information as an object of determination. In addition, the "predetermined numerical range" includes, when a value serving as a standard, such as the upper limit, is set, an aspect in which a numerical value serving as an object of determination is determined to be abnormal if equal to or higher than the upper limit, and an aspect in which the numerical value is determined to be abnormal if higher than the upper limit.

When, in the determination step, formulas (1) and (2) below, expressed by using the mean $\mu$, standard deviation $\sigma$, and n and m greater than 0, are set to the lower limit and the upper limit, respectively, and it is determined whether or not the input predetermined vital information is an abnormal value based on at least one of the lower limit and the upper limit, the determination standard can be set such that the numerical value distanced from the mean $\mu$ by $n\sigma$ in a positive direction is the lower limit and the numerical value distanced from the mean $\mu$ by $m\sigma$ is the upper limit.

$$\mu - n\sigma \qquad \text{formula (1)}$$

$$\mu + m\sigma \qquad \text{formula (2)}$$

That is, the value obtained by subtracting $n\sigma$ from the mean $\mu$ is set to the lower limit value and the value obtained by adding $m\sigma$ to the mean $\mu$ is set to the upper limit value, and based on at least one thereof, it can be determined whether or not the vital information is an abnormal value. In addition, the values of n and m may be a number greater than 0 as described above, and the values of n and m can be appropriately set in consideration of various conditions, such as strictness of determination standard, type of vital, past medical history of a subject, and the like. When the vital information is normally distributed, approximately 95% of vital information is distributed in the range of $\mu\pm2\sigma$, which can be adopted as an example of the determination standard. The "at least one of the lower limit and the upper limit" includes an aspect in which only the lower limit or only the upper limit is set as a standard, as well as an aspect in which both the lower limit and the upper limit are adopted as a standard.

Advantageous Effects

The software, the health condition determination apparatus, and the health condition determination method according to the present invention can realize "personal management" based on the intra-subject variation by reflecting vital signs considering individual differences of a subject or daily conditions of the subject to accurately understand health condition of the subject under intense heat or cold environments.

BRIEF DESCRIPTION OF THE DRAWINGS

FIG. 8 is a schematic diagram showing an example of an input screen of vital sign values.

FIG. 9 is a schematic diagram showing another example of an input screen of vital sign values.

FIG. 12(a) is a graph showing a Q-Q plot of standard deviation in the body temperature, and FIG. 12(b) is a graph showing a Q-Q plot of standard deviation in the systolic blood pressure.

FIG. 13(a) is a graph showing a Q-Q plot of standard deviation in the respiration rate, and FIG. 13(b) is a graph showing a Q-Q plot of standard deviation in the oxygen concentration (oxygen saturation).

FIG. 16 is a schematic diagram showing an example of a condition panel.

MODE FOR CARRYING OUT THE INVENTION

Hereinafter, embodiments of the present invention will be described with reference to the drawings, and provided for the understanding of the present invention.

Figure 1:
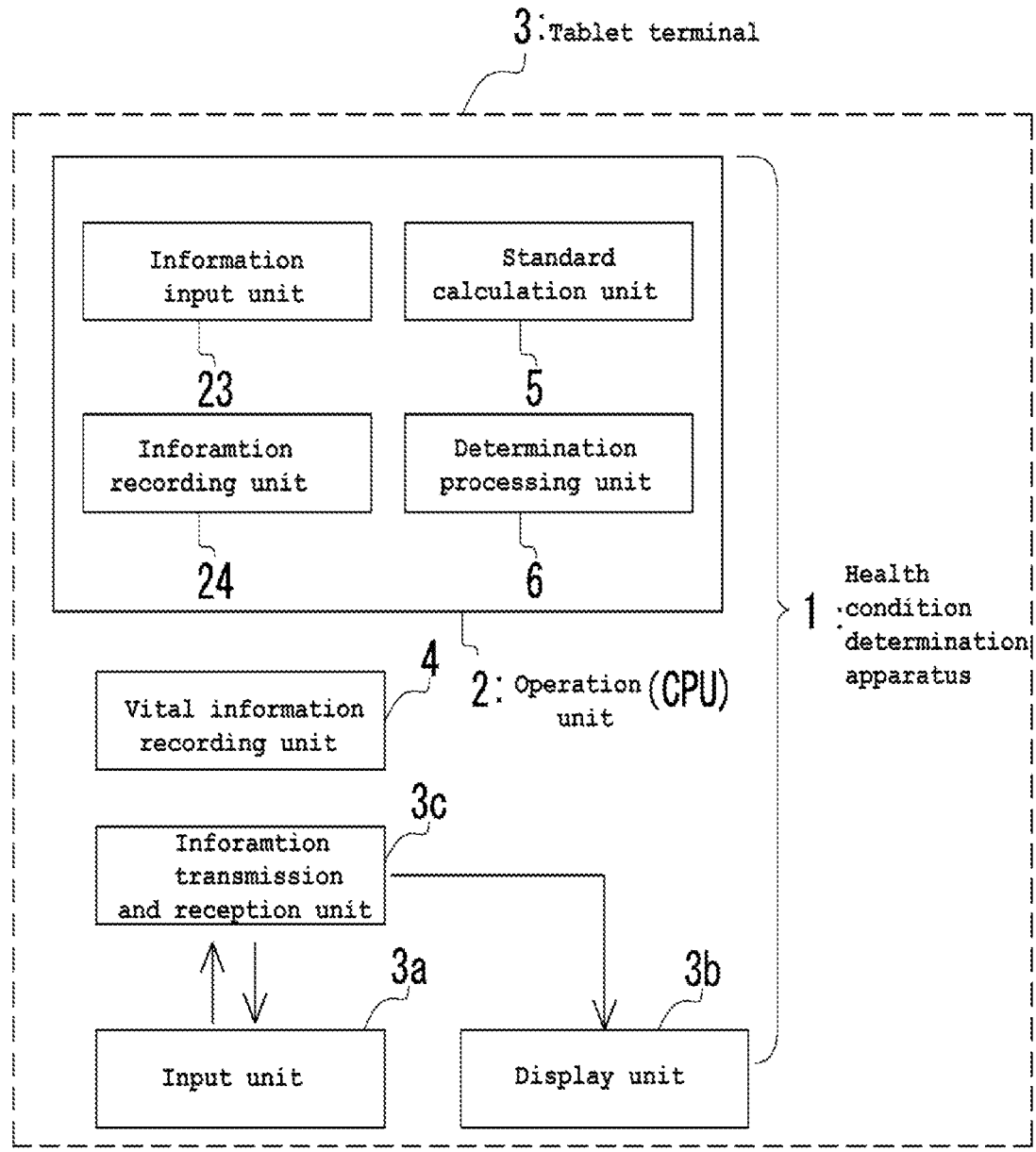
FIG. 1 is a diagram showing a schematic configuration of a tablet terminal into which a software adapting the present invention is introduced (first system configuration).

FIG. 1 is a diagram showing a schematic configuration of a tablet terminal into which a software employing the present invention is introduced. In addition, the structure shown below is an example of the present invention, and the content of the present invention is not limited thereto.

[1. Entire Configuration of Apparatus]

A software employing the present invention can be introduced into a general-purpose information processing device and gives an embedded information process device each piece of information processing function necessary for implementing the present invention. As a result, a tablet terminal 3 can make a determination of health condition reflecting an intra-subject variation in a value of a vital sign of a subject.

The information processing device includes a computation unit such as a CPU, a memory unit such as a RAM or a ROM, a display screen, such as a liquid crystal screen, an input unit, such as a keyboard, a communication unit for controlling the communication with the Internet or the like. Examples thereof are a general-purpose personal computer, a tablet terminal, a smartphone, and the like. Further examples of the information processing device are various medical care devices, medical systems and nursing care systems installed in hospitals and facilities, and the like, and a software employing the present invention is embedded therein for use.

The software employing the present invention, which is an application software, is downloaded and embedded in the tablet terminal 3, and a tablet terminal having a health condition determination function is a health condition determination apparatus 1.

Hereinafter, it is assumed that a user of the health condition determination apparatus 1, that is, a person whose health condition is determined is referred to as "subject".

As shown in FIG. 1, the health condition determination apparatus 1 (tablet terminal 3) has an operation unit 2. The operation unit 2 is a processing unit performing each information processing function of the health condition determination apparatus 1. That is, the software employing the present invention allows the operation unit 2 of the tablet terminal 3 to function as an information input unit 23, an information recording unit 24, a standard calculation unit 5, a determination processing unit 6, and the like. Through the processing function of each of the units, the transmission and reception of information, recording of information, determination of normality or abnormality, setting of determination standards, notification of determination result, creation and display of display information, and the like are carried out. In addition, the tablet terminal 3 is accessible to an external server, a terminal, and the like via the Internet, and can carry out of the transmission and reception of information to and from an external server, a terminal, or the like. The information recording unit 24, the standard calculation unit 5, and the determination processing unit 6 are examples of "information recording unit", "standard calculation unit", and "determination unit" in the present claims, respectively.

The tablet terminal 3 has a vital information recording unit 4, an information transmission and reception unit 3*c*, an input unit 3*a*, and a display screen 3*b*.

The information transmission and reception unit 3*c* is responsible for transmission and reception of information among the operation unit 2, the vital information recording unit 4, the input unit 3*a*, the display screen 3*b*, and the like. The information transmission and reception unit 3*c* may be configured to be able to perform the transmission and reception of information between the tablet terminal 3 and an external terminal.

Herein, each piece of information processed by the software employing the present invention does not necessarily have to be recorded on the vital information recording unit 4 of the tablet terminal 3. For example, various types of information are transmitted to an external server or an external terminal via the information transmission and reception unit 3*c* of the tablet terminal 3 and are recorded therein, and thus necessary information can be received from an external server or the like at the time of determination or the like.

In other words, all the main elements of the health condition determination apparatus 1 need not be downloaded in the tablet terminal 3. For example, the tablet terminal 3 may perform only the display of display information, such as determination result information, a normal distribution curve, and a body temperature table, an external server, or the like may perform the recording of various types of information, determination processing, and the like.

The software employing the present invention may have a plurality of variations in the configuration of systems. Hereinafter, examples of several variations are described.

(First System Configuration)

The schematic configuration of the tablet terminal 3 shown in FIG. 1 allows the terminal alone to achieve the input, record, and determination of vital information, the display of determination results, and the setting of a determination calculation standard, by introducing the software employing the present invention into the terminal. That is, the apparatus alone can perform the functions of the present invention. The schematic configuration shown in FIG. 1 shows the use of a software employing the present invention in a "stand alone type" apparatus, which is not connected to the Internet environment. Information processing devices, which are not connected to the Internet environment, for example, various medical care devices, medical systems and nursing care systems, such as hospitals, and the like can be used as devices for exclusive use, through the introduction of the software of the present invention thereto. In this case, the connection to the Internet environment can be attained since the tablet terminal 3 has been described as an example of the information processing device. However, a health condition can be determined through only internal functions of the tablet terminal 3 as long as the tablet terminal 3 has a configuration shown in FIG. 1.

(Second System Configuration)

Figure 2:
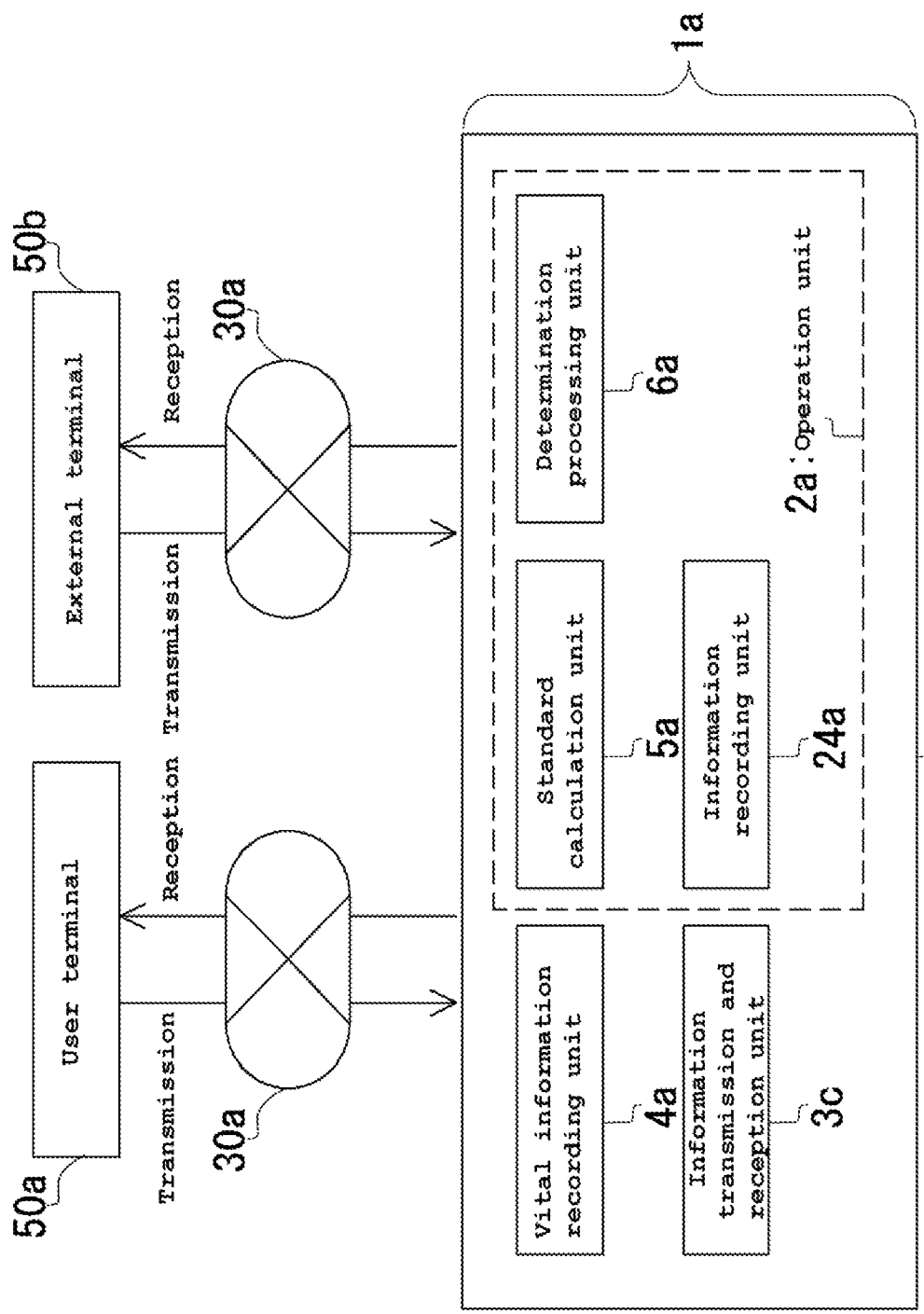
FIG. 2 is schematic diagram showing a second system configuration having a software employing the present invention.

FIG. 2 shows a second system configuration, which may allow an external serve to adopt functions of a software 1*a* employing the present invention. Here, a user terminal 50*a* or an external terminal 50*b* can access an information management server 32*a* via the Internet 30*a*. The information management server 32*a* is, for example, an external server provided in the form of a cloud, and the functions of the software 1*a* employing the present invention may be used on the information management server 32*a*.

The information management server 2*a* has a vital information recording unit 4*a*, an information transmission/reception unit 3*c*, and an operation unit 2*a*. The operation unit 2*a* has a standard calculation unit 5*a* and a determination processing unit 6*a*. The input of vital information is carried out through the user terminal 50*a* or the external terminal 50*b*, and the information input from each terminal is transmitted to the information management server 32*a*, and then the information management server 32*a* performs the record of information and the determination of health state. The determination results and the recorded information can be transmitted to the user terminal 50*a* or the external terminal 50*b*, and confirmed by each terminal. In this manner, the external server may employ a system configuration with the functions of the software 1*a*.

(Third System Configuration)

Figure 3:
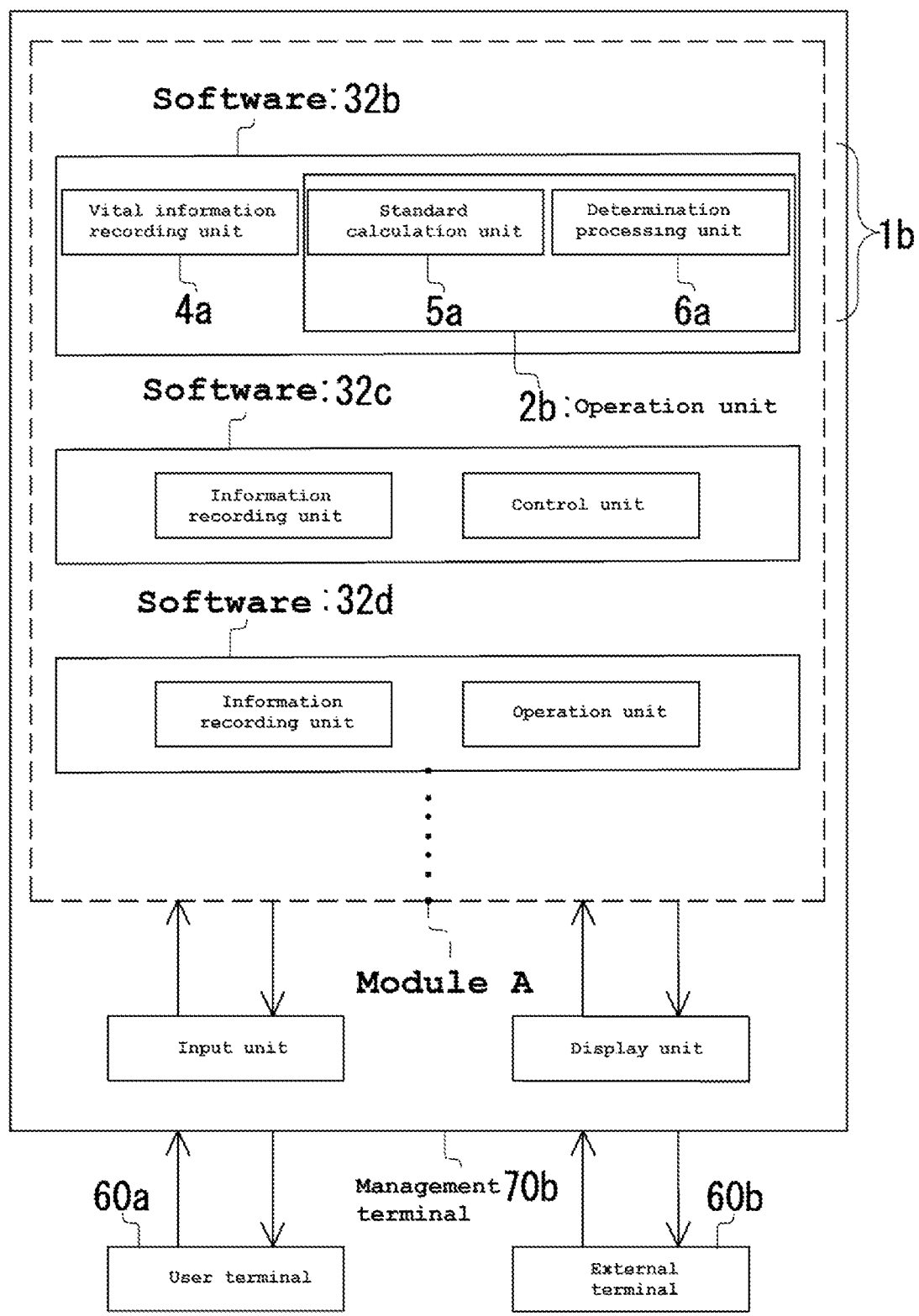
FIG. 3 is schematic diagram showing a third system configuration having a software employing the present invention.

FIG. 3 shows, as a third system configuration, a configuration of a management terminal 70*b* provided with module A having a plurality of softwares 32*c* and 32*d* in addition to the functions of a software 32*b* employing the present invention. The software 32*b* employing the present invention, together with the other softwares for executing various functions on the management terminal 70*b*, different therefrom, constitute one module A. That is, the software 32*b* can function while being embedded to function in module A of the management terminal 70*b* into which a plurality of softwares 32*c* and 32*d* have already been introduced. For example, the software employing the present invention can be embedded in a module provided in a management terminal of a medical system, such as an electronic carte.

In this third system configuration, vital information is input to the management terminal 70*b* to result in the determination of health condition, and the resulting information can be confirmed on the management terminal 70*b*. In addition, the user terminal 60*a* or the external terminal 60*b* is connected to the management terminal 70*b*, so that vital information is input from the user terminal 60*a* and transmitted to the external terminal 60*b*, and thus the determination of health condition is carried out in the management terminal 70*b*, and the resulting information can be confirmed through the reception of the user terminal 60*a* or the external terminal 60*b*. As such, the software employing the present invention may adopt a configuration of functioning as a part of a module composed of a plurality of softwares.

As described above, the system configuration of the software (or health condition determination apparatus) employing the present invention has a plurality of variations. Although three examples have been described above, the configuration of the software (or health condition determination apparatus) employing the present invention is not limited thereto. For example, the vital information recording unit may be installed in the user terminal and the standard calculation unit and the determination processing unit are provided in the external server, and thus members with necessary functions may be divided into the terminal and the server. That is, various configurations may be adopted as long as vital information of a subject is recorded, a determination standard reflecting the intra-subject variation is set, and the determination of health condition can be performed.

The description of the detailed configuration will be continued by using a usage pattern of the tablet terminal 3 shown in FIG. 1.

[2. Vital Information Recording Unit]

Figure 4:
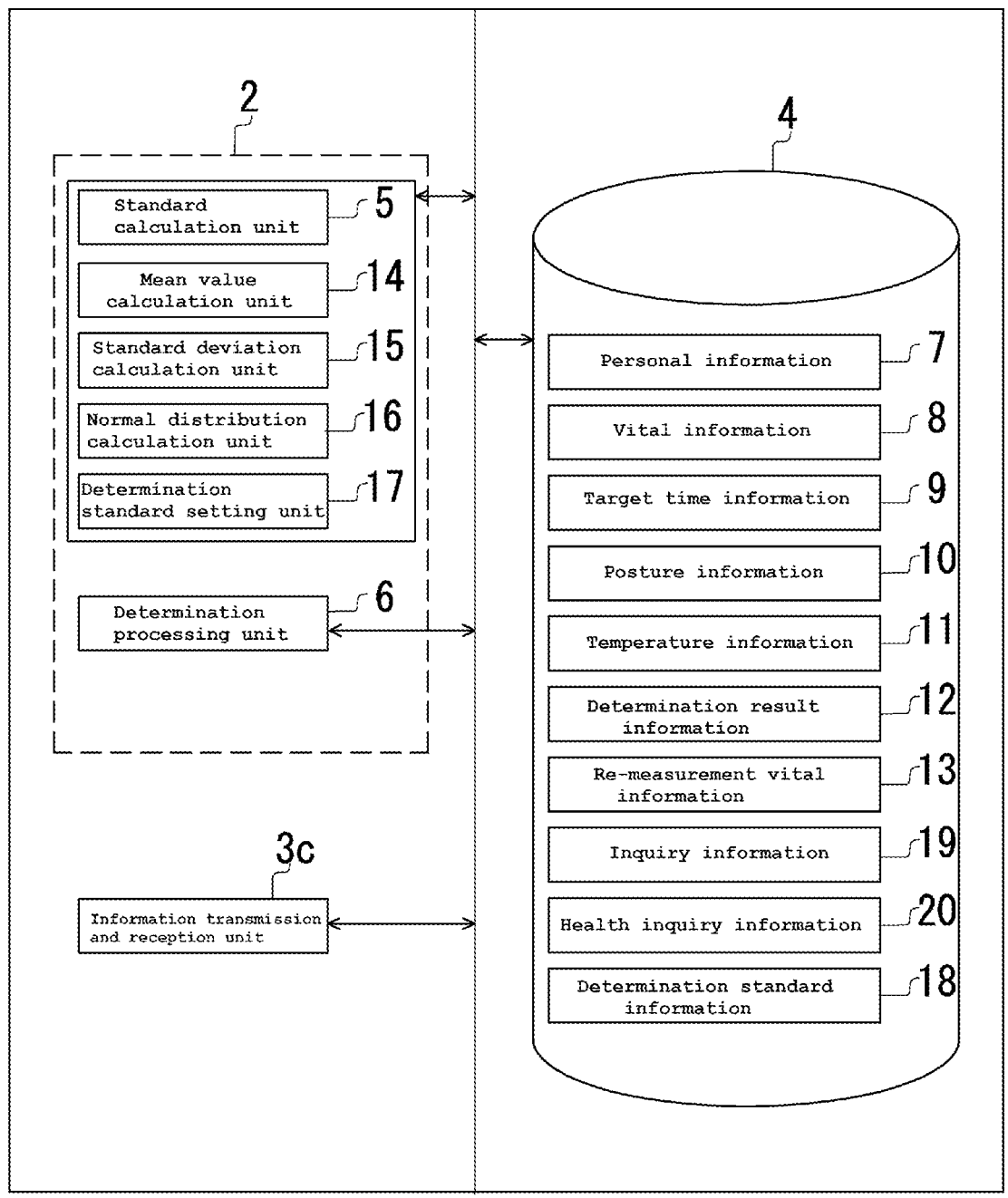
FIG. 4 is a block diagram showing a configuration of an operation unit, an information transmission and reception unit, and a vital information recording unit.

As shown in FIG. 4, various types of information are recorded on the vital information recording unit 4.

The vital information recording unit 4 is a unit on which personal information of subjects and vital information of the subjects, measured by various vital measurement instruments, together with measurement date information, are recorded. Various types of information recorded on the vital information recording unit 4 can be input or corrected through the input unit 3a, the information transmission and reception unit 3c, and the information input unit 24 (not shown) of the tablet terminal 3. In addition, the content of various types of information recorded on the vital information recording unit 4 can be confirmed through the display screen 3b and the information transmission and reception unit 3c of the tablet terminal 3.

The personal information 7 of a subject and vital information 8 are recorded on the vital information recording unit 4, the vital information including measurement values of vital signs measured by respective vital measurement instruments and measurement date and time information. The personal information 7 and the vital information 8 are configured so as to be recorded in connection with identification information capable of identifying individual subjects. Therefore, a plurality of subjects can be identified, and one health condition determination apparatus 1 can be used for a plurality of subjects.

The vital information 8 contains body temperature, pulse rate, systolic blood pressure, diastolic blood pressure, and respiration rate. The measurement date and time contained in the vital information 8 refers to the date and time when a subject performs vital measurement, and for example, a subject input the time confirmed when the subject performs vital measurement.

Here, the types of vital information 8 is not necessarily limited to body temperature, pulse rate, systolic blood pressure, diastolic blood pressure, and respiration rate, but may be used for determination, including other vital signs. The vital information may include the rate of breathing. The adoption of other vital signs, such as oxygen saturation, is also considered. However, the above examples are the basic vital signs, and the obtaining of the vital information is also simple, and thus it is preferable to adopt the vital information of body temperature, pulse rate, systolic blood pressure, diastolic blood pressure, and respiration rate.

In addition, the vital measurement instruments for measuring vital information are not particularly limited, and any vital measurement instrument is sufficient as long as it can measure body temperature, pulse, systolic blood pressure, diastolic blood pressure, and respiration rate. For example, a home vital measurement instrument may be favorable as long as it can perform vital measurement. In other words, the use of a viral measurement instrument is not necessary if vital information can be obtained. For example, the pulse rate or respiration rate per minute is measured while the time is measured with a clock, and this measurement value can be used as vital information. However, in an aspect of accurately understanding the intra-subject variation of vital information, it is preferable that the vital information is obtained in the same manner. There is a bias in the method of obtaining vital information if the kind of vital measurement instrument is changed frequently or the measurement by a vital measurement instrument and the measurement without a vital measurement instrument are coexist in daily measurements. Therefore, it is preferable to obtain vital information using the same manner or the same vital measurement instrument.

The vital Information (8) is obtained by recording vital information measured twice a day (in the morning and evening). Also, target time information 9, which is information of the target time at which a subject performs vital measurement, can be recorded on the vital information recording unit 4. The target time information 9 is obtained by recording a target time at which a subject performs vital measurement, for example, at 8:30 in the morning or at 18:00 in the evening. The target time information 9 may be freely set and corrected by a subject.

Posture information 10, which is information of good posture when each vital sign is measured, is recorded on the vital information recording unit 4. The posture information 10 is, for example, as follows.

(1) Body temperature For example, when the body temperature is measured using a thermometer measuring the body temperature under the armpit, the body information is directed to information as to "whether a measurement portion of the thermometer is located at the center of the armpit", "whether the armpit and the thermometer are in close contact with each other", "whether a subject is in the same posture every time", and the like.

(2) Pulse rate For example, when the pulse rate is measured by placing an electronic pulse system or a finger on the wrist, the posture information is directed to "whether a subject is in a stable state", "whether a subject is in a comfortable relaxed posture", "whether a subject is in the same posture every time", and the like.

(3) Systolic blood pressure and diastolic blood pressure For example, when the measurement is performed by an oscillometric method using vascular vibration, the posture information is directed to "whether a subject is in a stable state", "whether the arm or wrist wound by the cuff is located at the height of the heart", "whether is in the same posture every time", and the like.

Here, the vital information 8 is not necessarily configured such that the vital information measured twice a day (in the morning and evening) is recorded, and the measurement may be performed once a day. The number of times of vital information recording a day is not limited as long as, as will be described later, a predetermined number of data, used in the calculation of the standard by a standard calculation unit, or the calculation of the vital mean value and the vital standard deviation used for the calculation of the standard of the determination, are recorded. Also, the vital information need not be recorded every day, and there may be a day when vital information is not recorded. Here, in an aspect of properly understanding the intra-subject variation in the same subject, it is preferable that the vital information is recorded every second in a broad sense, and the vial information is recorded once to 24 times a day. Also, the information is easy to record with only manual vital measurement, the variation of a vital sign value on the same day can be confirmed, and comparison with the measurement information on a different day is easy, so that it is more preferable that the vital information measured twice a day (in the morning and evening) can be recorded.

The target time information 9 does not necessarily have to be recorded on the vital information recording unit 4. However, in an aspect that, as will be described later, by recording the target time information 9, the vital information measured by a subject, deviating from the time recorded in the target time information 9, is excluded from the calculation basis, such as vital mean value, for determination, thereby improving the accuracy of determination, it is preferable that the target time information 9 is recorded on the vital information recording unit 4.

The posture information 10 does not necessarily have to be recorded on the vital information recording unit 4. However, in an aspect that, as will be described later, by recording the posture information 10, when the vital information of a subject is determined to be an abnormal value, the display screen 3b of the tablet terminal 3 displays "Did you measure with correct posture?" together with posture information 10 of vital signs as the basis of the determination, thereby warning the posture for vital measurement or pressing vital re-measurement. As a result, the accuracy of vital measurement or the reliability of determination of vital measurement can be improved. Therefore, it is preferable that the posture information 10 is recorded on the vital information recording unit 4.

In addition, the measurement methods of respective vital signs and the posture information 10 are not limited to those described above, and the vital measurement methods or the posture information 10 suitable therefor can be appropriately changed.

Temperature information 11 of a place of vital measurement can be recorded on the vital information recording unit 4. The temperature information 11 is recorded in connection with the records at the time of each measurement of the vital information 8. For example, information of the temperature of a measurement place, which is confirmed and input by a subject, is adopted as the body temperature information 11.

Here, the body temperature information 11 of a place of vital measurement does not necessarily have to be recorded on the vital information recording unit 4. However, as will be described later, when, through the comparison of the temperature information on the day of determination with the temperature information in the vital measurement on the previous day, the displacement between the two types of temperature information exceeds a predetermined range, the vital information on the day of determination can be excluded from the calculation basis of the subsequent vital mean value or the vital standard deviation. As a result, the influence of the body temperature on the variation of the vital information can be reduced, and thus the accuracy of determination can be increased. Therefore, it is preferable that the temperature information 11 of a place of vital measurement is recorded on the vital information recording unit 4.

Each piece of vital information is input to the vital information recording unit 4, and determination result information 12, which is information as a result of determination as to whether or not the determination processing unit 6 determines the vital information to be an abnormal value, can be recorded on the vital information recording unit 4.

In addition, vital information when the re-measurement is performed for vital measurement and re-measurement vital information 13, which is information of date at the time of measurement, can be recorded as the vital information 8 in the vital information recording unit 4. The details of the re-measurement of the vital information will be described later, but for example, the re-measurement vital information mean the vital information of re-measurement performed to investigate the accuracy of vital information when the determination processing unit 6 determines the vital information to be an abnormal value.

When each piece of vital information is displayed on the display screen 3b of the tablet terminal 3, characters indicating three pattern vital information, such as usual vital information recorded without re-measurement, vital information as an object of re-measurement, and vital information after re-measurement, are displayed in different colors.

Here, the determination result information 12 does not necessarily have to be recorded on the vital information recording unit 4. However, in an aspect that the determination result of the past vital information can be confirmed, the determination result information can be used as reference information for increasing the accuracy of determination, and the determination result information can be used in the comparison with doctor's diagnosis results or in the conjunction with a medical system, it is preferable that the determination result information 12 can be recorded on the vital information recording unit 4.

Here, the re-measurement vital information 13 does not necessarily have to be recorded on the vital information recording unit 4. However, considering that, as will be described later, the verification as to whether or not the vital measurement is correct can be attained by using the re-measurement vital information 13 or the calculation of the subsequent vital mean value or vital standard deviation can be attained by using the re-measurement vital information 13, it is preferable that the re-measurement vital information 13 is recorded on the vital information recording unit 4.

[3. Standard Calculation Unit]

The standard calculation unit 5 will be described. The standard calculation unit 5 is one of the functions that the software employing the present invention is executed by the calculation section 2. The standard calculation unit 5 performs, based on various types of information recorded on the vital information recording unit 4, the calculation of the determination standard for determination of vital information or the calculation of the vital mean value and the vital standard deviation used for the calculation of the determination standard. In addition, a normal distribution is calculated based on the vital mean value and the vital standard deviation by the standard calculation unit 5.

Various types of information calculated or recorded by functioning of the operation unit 2 as the standard calculation unit 5 can be added or corrected through the input unit 3a and the information transmission and reception unit 3c of the tablet terminal 3 and the information input unit 24 of the operation unit 2. In addition, various types of information calculated or recorded by functioning of the operation unit 2 as the standard calculation unit 5 can be confirmed through the display screen 3b of the tablet terminal 3.

FIG. 4 shows the execution of the software employing the present invention in the operation unit 2. The operation unit 2 functions as a mean value calculation unit 14, a standard deviation calculation unit 15, a normal distribution calculation unit 15, and a determination standard setting unit 17, in addition to as a standard calculation unit 5. The mean value calculation unit 14 and the standard deviation calculation unit 15 calculate "mean value of vital information" for a predetermined period from record information of the same period and "standard deviation of vital information" in a statistic distribution of vital information of the same period, respectively, based on the vital information 8 and the re-measurement vital information 13 recorded on the vital information recording unit 4.

In addition, the normal distribution calculation unit 16 calculates a normal distribution from the mean value and the standard deviation of vital information for a predetermined period. The calculated normal distribution from the mean value and the standard deviation of vital information is recorded in connection with the determination result information 12 on the day of determination in the vital information recording unit 4.

Hereinafter, the mean value of vital information is referred to as "vital information mean value" and the standard deviation of vital information is referred to as "vital information standard deviation", except for a case of indicating the name of a mean value or standard deviation of a kind that performs a particular calculation.

In addition, the determination standard setting unit 17 creates determination standard information 18 used in the determination by the determination processing unit 6, based on the vital mean value and the vital standard deviation calculated by each calculation unit, in conjunction with the mean value calculation unit 17 and the standard deviation calculation unit 15. The created determination standard information 18 is recorded on the vital information recording unit 4. The details of the calculation and creation of the vital mean value, the vital standard deviation, and the determination standard information 18 and the plurality of settings are described in the following item "5. Calculation and determination of vital mean value and vital standard deviation".

For "predetermined period", which is employed in the calculation of the average value calculation unit 14 and the standard deviation calculation unit 15, a method of using vital information for 90 days starting from the day of determination is typically adopted. The vital information for this period includes vital information 8 and re-measurement vital information 13 for the past 90 days including the day of determination.

As described above, the vital information measured twice a day in the morning and evening can be recorded as the vital information 8. When the operation unit 2 functions as the average value calculation unit 14 and the standard deviation calculation unit 15 to calculate the vital mean value and the vital standard deviation, the mean value on the day of measurement, calculated from the vital information twice a day, is set to be processed as vital information on the day of measurement. In other words, when the vital mean value and the vital standard deviation are calculated, for data of the vital information for one day in a predetermined time, one piece of vital information (mean value of morning and evening measurements) is used for one kind of vital sign.

In addition, the mean value calculation unit 14 and the standard deviation calculation unit 15 calculate a vital information mean value and a vital information standard deviation for the day of determination, referring to the vital information 8 and re-measurement vital information 13 recorded before the day of determination, at the time of determination of vital information of a subject. As a result, the determination standard used by the determination processing unit 6 is revised every day of determination, and the intra-subject variation of the vital information of a subject is easily reflected on the determination as to whether or not the vital information is an abnormal value.

Here, "predetermined period", which is adopted in the calculation by the mean value calculation unit 14 and the standard deviation calculation unit 15, does not need to use vital information for 90 days starting from the day of determination. Here, every day for a predetermined period can be appropriately set and changed. However, in order to understand the intra-subject variation of vital information of a subject, a predetermined number of days of vital information are required, and the predetermined number of days is preferably 90 days.

In addition, a predetermined period is divided into 90 days, so that the intra-subject variation of unique vital information during the period may be used. For example, the vital information limited to sections for each season with different weather and temperature conditions is used, so that the vital information reflecting the intra-subject variation of a subject in each season can be determined.

In an aspect, the period of using the vital information is 90 days or more, and for a longer period, for example, after the subject starts to use the health condition determination apparatus 1, the vital information 8 and re-measurement vital information 13) for a total period may be used. As a result, the information of vital measurement accumulated over a long period can be used for vital information of the same subject, and the intra-subject variation of the vital information of the subject can be more easily reflected in the determination as to whether or not the vital information is an abnormal value. In addition, the minimum number of days for understanding the intra-subject variation is 30 days or more in the number of data.

The number of days of the "predetermined period" employed in the calculation by the mean value calculation unit 14 and the standard deviation calculation unit 15 is, for example, 2-3650 days, preferably 7-365 days, and more preferably "90 days". Especially, the adoption of 90 days as the number of days makes it easy to appropriately understand the intra-subject variation of the same subject.

Figure 5:
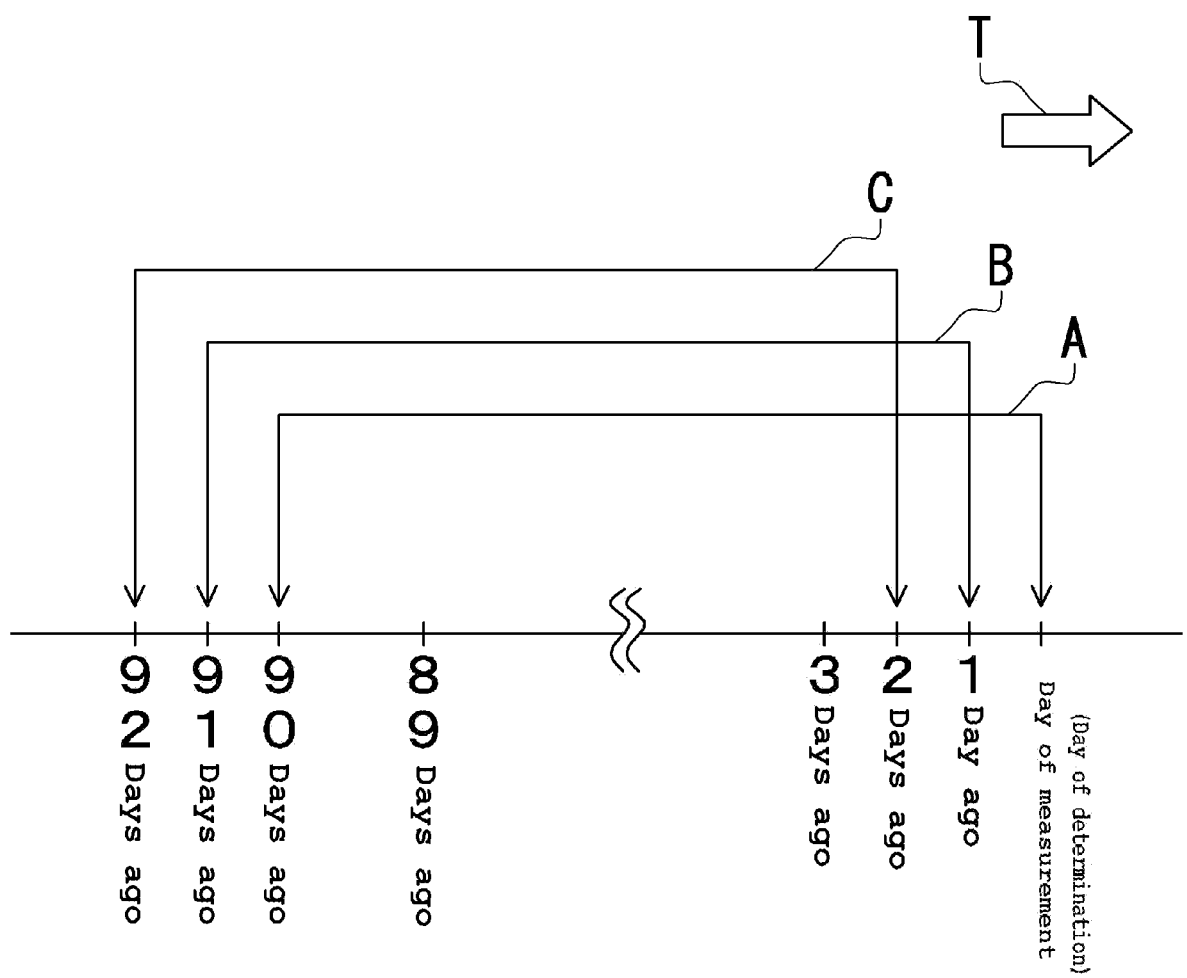
FIG. 5 is a schematic diagram showing an example of the setting of a calculation period of vital mean value and vital standard deviation.

When "90 days" is employed as the "predetermined period" employed in the calculation by the mean value calculation unit 14 and the standard deviation calculation unit 15, this calculation period is set such that the range of 90 days is shifted by one day with the lapse of time, as show in FIG. 5. That is, the 90-day period used for calculation at a certain day of measurement (day of determination) is expressed as a range from the ninety days before the day of measurement to the day of measurement including the day of measurement (symbol A). Alternatively, "predetermined period" used for calculation one day before the day of measurement is expressed as a range from 91 days before the day of measurement to one day before the day of measurement (symbol B). Alternatively, "predetermined period" used for calculation two days before the day of measurement is expressed as a range from 92 days before the day of measurement to two days before the day of measurement (symbol C). As such, the 90-day range of "predetermined period" can be set to be shifted by one day with the lapse of time (the arrow direction by symbol T).

Here, "predetermined period" employed in the calculation by the mean value calculation unit 14 and the standard deviation calculation unit 15 is set to use the vital information for 90 days including the day of determination, but the day of determination does not need necessarily to be a start point. For example, the vital information for 90 days starting from the previous day of the day of determination, except for the day of determination, can be set to be used. However, the inclusion of the day of determination can reflect the recent condition of the same subject, so that the intra-subject variation of the subject can be easily understood, and therefore, it is preferable to use the vital information for 90 days including the day of determination, as "predetermined period" employed in the calculation of the mean value calculation unit 14 an the standard deviation calculation unit 15.

Here, "predetermined period" employed in the calculation by the mean value calculation unit 14 and the standard deviation calculation unit 15 does not need to vital information measured during consecutive days. For example, in a case where there is a day without vital measurement by a subject and thus there is a day without the record of vital information, the total number of days in a predetermined period may be 90 days.

Figure 6:
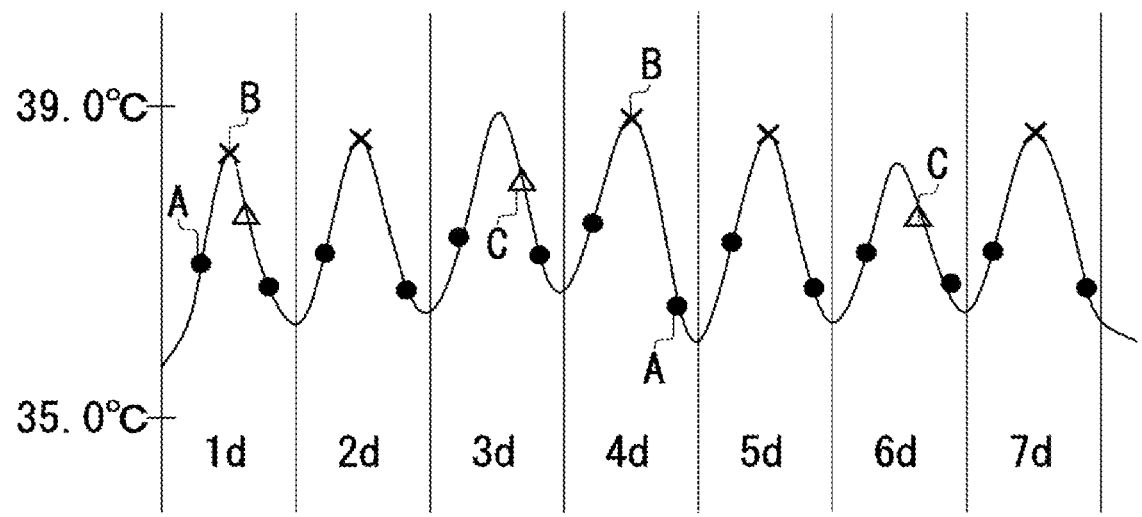
FIG. 6 is a schematic diagram showing an extraction example of vital information.

For example, in the above-described configuration, as indicated by symbol A (black circles) in FIG. 6, vital information is recorded twice in the morning and afternoon on consecutive days, and all the information is used in the calculation by the mean value calculation unit and the standard deviation calculation unit 15.

Here, in the present invention, the vital information does not necessarily need to be obtained on consecutive days as long as the number of data of the vital information for the set number of days is provided. In an aspect, as shown in the vital information indicated by symbol B (figure X) or symbol C (white triangle) in FIG. 6, the vital information may be obtained once for several days if the vital information is obtained on non-consecutive days. In an aspect, the vital information may be partially extracted based on the set condition in a state in which vital information is consecutively recorded. The set condition is, for example, extracting only vital information every Monday, extracting only the vital information obtained in the morning, or extracting only a predetermined data.

When the vital mean value and the vital standard deviation are calculated by the mean value calculation unit 14 and the standard deviation calculation unit 15, the mean value on the day of measurement calculated from the vital information twice a day does not necessarily need to be set to be processed as vital information on the day of measurement. For example, in the case where the vital information measured "in the morning" on a certain day of determination is determined, the vital mean value and the vital standard deviation may be calculated by using only the vital information 8 and the re-measurement vital information 13 recorded in the morning on the day of measurement. Thus, the standard set based on the vital mean value and the vital standard deviation from the vital information recorded in the morning on the day of measurement may be adopted as the determination standard used by the determination processing unit 6. The measurement data in the afternoon may also be processed in the same manner.

The normal distribution calculation unit 16 is an example of a display information creation unit of the present invention. As described above, the normal distribution calculation unit 16 is a part which a normal distribution is calculated from the mean value and the standard variation of vital information for a predetermined period. A normal distribution at each day of determination of a subject can be calculated; a normal distribution curve is created by graphing a probability density function of the calculated normal distribution; and this normal distribution curve is displayed on the display screen 3b of the tablet terminal 3.

[4. Determination Processing Unit]

The determination processing unit 6 will be described. The determination processing unit 6 is one of the functions that are performed by the operation unit 2 through the software employing the present invention. The determination processing unit performs a determination processing as to whether or not the vital information on the day of determination, input through the input unit 3a of the tablet terminal 3, is an abnormal value, based on the determination standard information 18 set by the processing of the mean value calculation unit 14, the standard deviation calculation unit 15, and the determination standard setting unit 17. The determination result information 12, which is a determination result from the determination by the determination processing unit 6, is recorded on the vital information recording unit 4 as described above. In addition, the content of the determination result information 12 can be confirmed through the display screen 3b of the tablet terminal 3.

The determination processing unit 6 is configured to output the determination result information 12 in conjunction with the vital information recording unit 4 and the standard calculation unit 5. In addition, the determination result information 12 can be confirmed on the display screen 3b of the tablet terminal 3. The determination result information 12 can be confirmed on screens of an external server or an external terminal after the determination result information 12 is transmitted to the external server or the external terminal through the information transmission and reception unit 3c of the tablet terminal 3, as well as the display screen 3b of the tablet terminal 3.

In addition, the determination result information 12 can be configured to notify a subject of a notification sound for notifying the determination result information 12 or a mail message, as well as can display the determination result information 12 on the display screen 3b of the tablet terminal 3. When the determination result information 12 is notified using a notification sound, for example, notification sounds for cases of an abnormal value or otherwise may be exchanged with each other.

The details of an apparatus or an input screen, which is used for functionalizing the software employing the present invention, will be described.

For example, as shown in FIG. 7(a), the vital information is obtained by a wearable type vital measurement instrument 21a or a thermometer 21b, and the measurement values obtained thereby, together with measurement time information, are input through a screen displayed on the display screen 3b of the tablet terminal 3. A touch panel type input unit 3a is displayed on the display screen 3b, and vital information is input to the input unit 3a. In the case of the tablet terminal 3 into which the software employing the present invention is introduced (first system configuration), the terminal alone can perform the recording of information, the determination of health condition, and the display of the determination results.

Alternatively, in FIG. 7(b), a smartphone terminal 22a or a personal computer terminal 22b (hereinafter, referred to as "PC terminal") access an information management server 32a as the external server described in the above second system configuration, and an input of vital information from the smartphone terminal 22a or the PC terminal 22b can be performed thereon. The determination of health condition is performed by the information management server 32a based on the vital information transmitted from each terminal, and the information of the results is transmitted to each terminal, and displayed on the screen of each terminal.

Figure 9:
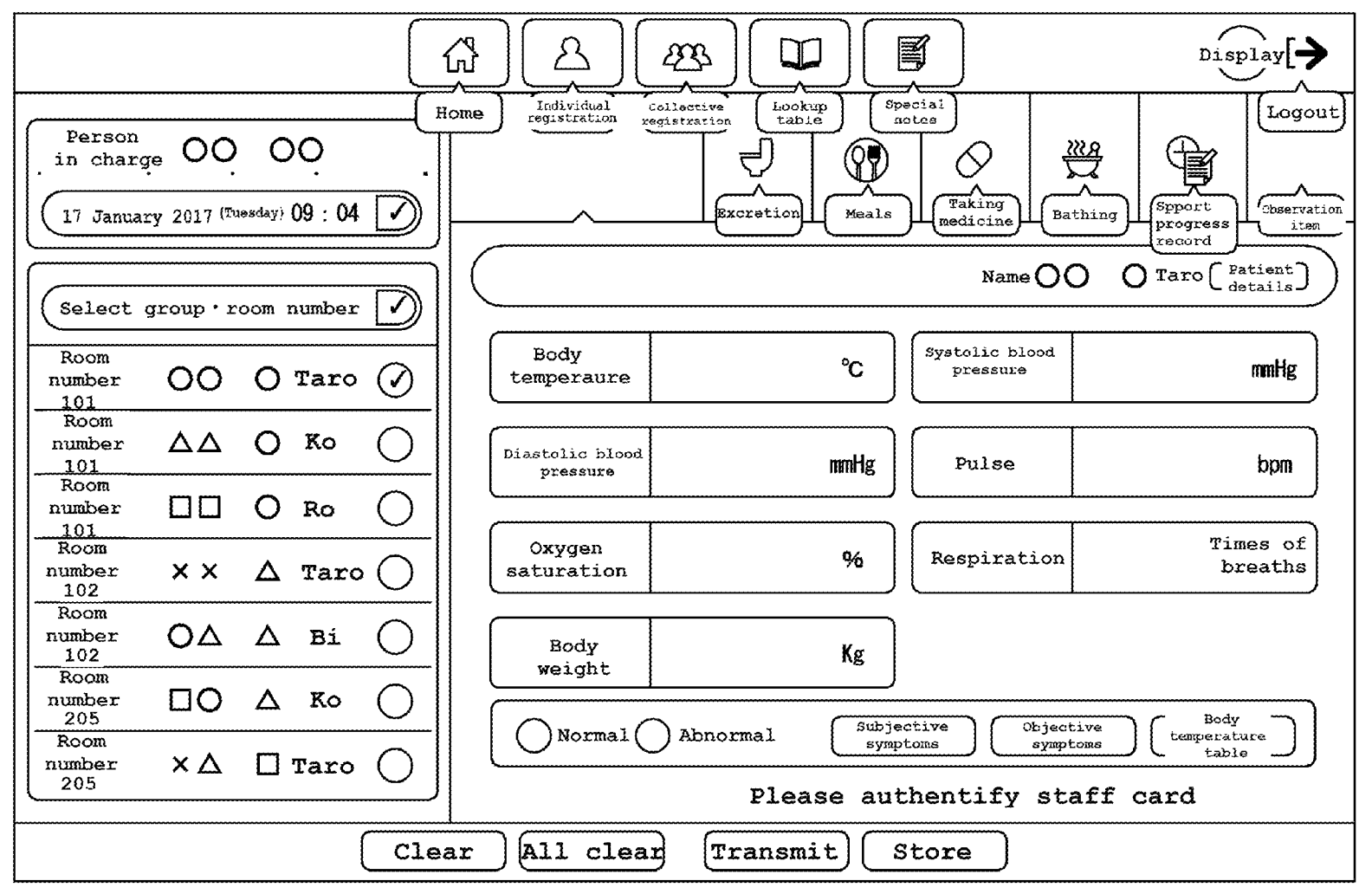

In addition, FIGS. 8 and 9 show input screens of the tablet terminal 3, the smartphone terminal 22a, and the PC terminal 22b. FIGS. 8 and 9 show examples of an input screen used when a patient in a hospital or a resident in a nursing facility or the like is a target of determination of health condition. In FIG. 8, input items of one person subject and a ten-key area displaying numbers are shown. There are name fields of a subject and a body temperature staff, and input fields of measurement data in body temperature, blood pressure (upper and lower), pulse rate, oxygen concentration, body weight, and respiration. The value of each vital sign can be input by operating the cursor on the touch panel or on the screen of the ten-key area.

In the screen display of FIG. 8, there are inquiry items of eating, urination, defecation, and observation, and a plurality of items for checking health condition of a subject, in addition to the vital signs. The plurality of items for checking health condition not only leave the records of daily health condition of a subject, but also is information usable in the calculation of the determination standard of vital information to be described later. The input information is recorded in the vital information inside the apparatus or transmitted to the external information management server 32 by touch or click of a transmission button.

In the input screen shown in FIG. 9, there are a plurality of input fields of measurement data of vital signs and selection items for normality or abnormality of the condition determined by a subject himself or herself, on the right side of the screen. In addition, the input screen is configured to confirm the vital change of a subject in a time sequence by selecting a subjective symptom, an objective symptom, and a body temperature table and inputting condition information. In the screen of FIG. 9, the names of a plurality of subjects are displayed. A name field is selected to display a screen of the selected subject. Also, time information at the time of inputting values of vital signs is input at the same time. In addition to the input screen of the values of the vital signs, information can be recorded or displayed on items regarding the registration of information or nursing items for providing excretion, mean, and the like.

As described above, the input screen when the software of the present invention is used enables input or the display of information in accordance with the related items, targeting a patient in a hospital or a resident in a nursing facility or the like. The display on the input screen is not limited to the content related to a caregiver, and for example, the input screen may have a screen configuration in which the input or recording of the values of respective vital signs is combined with the management of the information of body weight and the like, by an application software for health care. That is, there may be a mode that a healthy subject uses for daily health care.

A specific determination method based on vital information will be described.

[5. Calculation of Vital Mean Value and Vital Standard Deviation and Determination]

The vital mean value and the vital standard deviation are calculated based on the vital information 8 and the re-measurement vital information 13 recorded on the vital information recording unit 4, and here, the operation unit 2 functions as the mean value calculation unit 14 and the standard deviation calculation unit 15 of the standard calculation unit 5. In addition, the determination standard information 18 is set based on the vital mean value and the vital standard deviation. The following shows the determination standards of a plurality of patterns employed in the present invention and the determination content. Meanwhile, the determination standard setting unit 17 changes a setting, so that a determination method to be used can be appropriately selected or a method in which a plurality of patterns are combined can be selected.

[5-1. Calculation of all Vital Information]

First, as setting methods for the most basic vital mean value, the vital standard deviation, and the determination standard information 18 based thereon, there may be a method wherein the vital information 8 and the re-measurement vital information 13 recorded on the vital information recording unit 4 are used in the calculation of the vital mean value or the like. In the present method, the vital mean value and the standard deviation based on vital information are calculated using the following formulas (3) and (4) in the mean value calculation unit 14 and the standard deviation calculation unit 15.

$$\mu = (1/N) \times \Sigma Si \qquad \text{formula (3)}$$

$$\sigma = \sqrt{(1/N) \times \Sigma (Si-\mu)^2} \qquad \text{formula (4)}$$

Here, $\mu$ is the mean value of vital information, $Si$ is the measurement value of each piece of vital information, $N$ is the number of data of all vital information, and $\sigma$ is the standard deviation. $\Sigma Si$ represents the sum of measurement values of all vital information. The measurement value of each piece of vital information is the mean value of vital information twice a day (morning and evening) as described above. The content of all vital information recited herein may be obtained by extracting a part of the information recorded on the vital information recording unit 4 as described above.

When the vital information of a subject is determined at a certain day of measurement, the vital mean value $\mu$ and a first vital standard deviation $\sigma$ are calculated, using formulas (3) and (4) above, from data of the same subject, recorded on the vital information recording unit 4, based on the day of measurement. That is, the measurement standard is calculated including the values of vital signs, which is measured on the day of measurement and is the target of determination. Subsequently, the determination standard setting unit 17 uses a value represented by formula (1) or (2) below as the standard information 18.

$$\mu - n\sigma \qquad \text{formula (1)}$$

$$\mu + m\sigma \qquad \text{formula 1(2)}$$

Here, n and m are a number greater than 0.

In the determination standard information 18, a value represented by formula (1) above is the lower limit and a value represented by formula (2) above is the upper limit. When a value of predetermined vital information input from the tablet terminal 3 is equal to or smaller than the lower limit or equal to or greater than the upper limit value, the determination processing unit 6 determines the input predetermined vital information as "an abnormal value", and the determination result information 12 is displayed on the display screen 3b of the tablet terminal 3. Also, the determination result information 12 is recorded on the vital information recording unit 4.

In this determination, the vital mean value $\mu$ is a mean value calculated based on the variation of vital information of the same subject. That is, the vital mean value $\mu$ is a vital mean value in which the intra-subject variation of a subject is reflected during a period in which the vital information is recorded on the vital information recording unit 4 before the day of determination as a starting point. In addition, the vital standard deviation $\sigma$ calculated in formula (4) above, including the vital mean value $\mu$, reflects a deviation of the mean value of the vital information of a subject. In addition, the determination standard information 18 set in formula (1) or (2) above is calculated from the vital mean value $\mu$ and the vital standard deviation $\sigma$, and thus is, of course, a determination standard in which the intra-subject variation of a subject is reflected.

Here, n has been described to be a number greater than 0 in formula (1) or (2) as described above, but n and m may be decimals, such as 0.5, and natural numbers, such as 1 or 2. The setting of the values of n and m can be appropriately changed. For example, n and m are set such that $\mu - 1\sigma$ and µ+2σ are the lower limit and the upper limit, respectively, or µ−2σ and µ+1σ are the lower limit and the upper limit, respectively.

Considering various types of conditions, such as the setting of the lower limit and the upper limit, the accuracy required for the determination, the kind of vital to be determined, and the past medical history of a subject, n and m can be appropriately set. For example, n is 0.1-3, preferably 1-2, and most preferably 2.

Here, as an example of the setting of the lower limit and the upper limit, the use of µ±2σ in formulas (1) and (2) above will be described.

Figure 10:
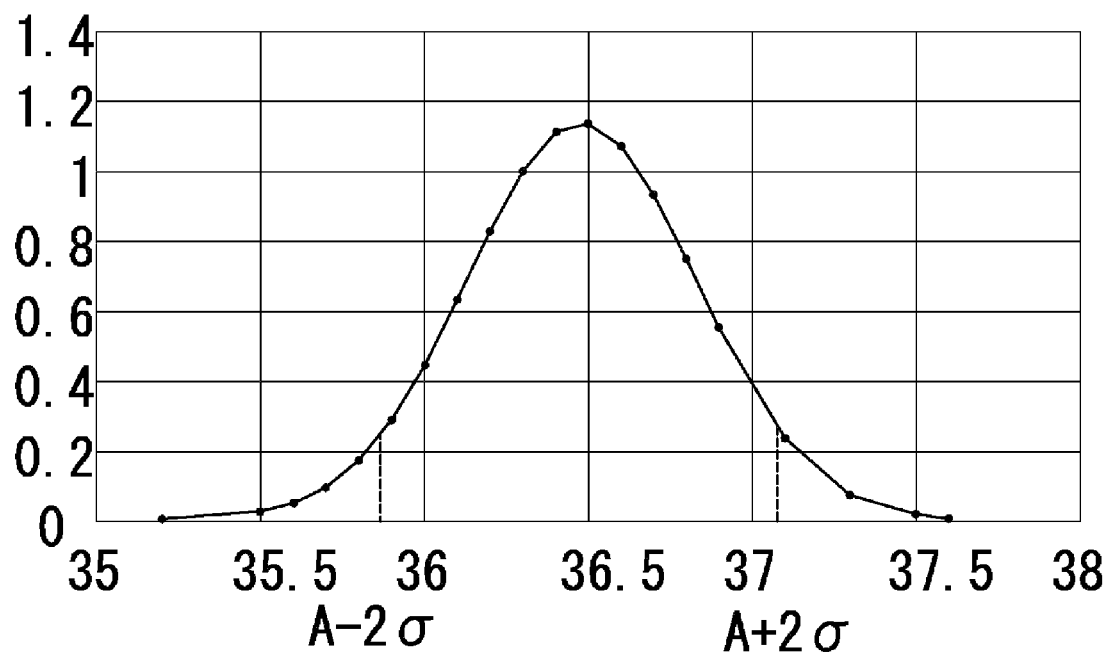
FIG. 10 is a graph showing an example of the determination standard by the vital mean value and the standard deviation in the body temperature.

FIG. 10 shows a graph of a normal distribution curve created by calculating the vital mean value (A) and the standard deviation (B) from the body temperature information for 90 days in a certain subject. The horizontal axis represents the probability variable of body temperature, and the vertical axis represents the probability density. In an example shown in FIG. 10, the vital mean value (A) is "approximately 36.48° C." and the standard deviation (σ) is "approximately 0.35". The value of "vital mean value+2σ" is "approximately 37.12 (expressed as A+2σ in FIG. 10)" and the value of "vital mean value−2σ" is "approximately 35.84 (expressed in A−2σ in FIG. 10)". That is, on this day of measurement, if the value of the standard body temperature or the monitored body temperature of the subject is equal to or higher than "37.12☐" or equal to or lower than "35.84☐", the determination processing unit 6 determine such a value as "an abnormal value".

Assuming that the vital information is normally distributed, approximately 95% of all vital information of a subject is distributed in the range of µ±2σ. Thus, if the vital information equal to or lower than the lower limit or equal to or higher than the upper limit is measured while µ±2σ is employed as the lower limit or the upper limit in the determination standard information 19, it can be estimated that the vital information in a distribution of only approximately 5% in the subject is measured. It is considered that when the vital information is included in a distribution of approximately 5%, a subject when the same vital information is measured can be determined to be in a condition of "an abnormal value" even based on the intra-subject variation. As such, the accuracy of determination can be statistically interpreted by employing µ±2σ for formulas (1) and (2) above.

In the description up to here, the determination by the determination standard information 18 is performed such that one type of determination results is obtained by determining the vital information equal to or lower than the lower limit or equal to or higher than the higher limit is "an abnormal value", but the determination results does not necessarily need to be delimited to one type. For example, the two-state lower limit or upper limit can be set by selecting a two-stage numerical value as a numerical value set for n or m in formulas (1) and (2) above. As a result, a two-stage determination can be performed while, for example, the vital information is determined as "there is a concern of attention" when the input vital information is equal to or lower than the first lower limit or equal to or higher than a first upper limit value close to the vital mean value, and the vital information is determined as "an abnormal value" when the input vital information is equal to or lower than the second lower limit or equal to or higher than the second upper limit, away from the vital mean value.

Further, in the above-described configuration, the determination is made as abnormality when the vital information, as an object of determination, is equal to or lower than the lower limit or equal to or higher than the upper limit, but a determination standard that is lower than the lower limit or higher than the upper limit may be employed.

As described above, a determination in which the intra-subject variation of the vital information of a subject is reflected can be performed by using the determination standard described in [5-1. Calculation using all vital information].

Here, a difference between a case where a distribution of vital information based on information of a different subject is created using vital information of the plurality of subjects and a case where a distribution of vital information of the same subject is created using vital information of the same subject will be described.

Figure 11:
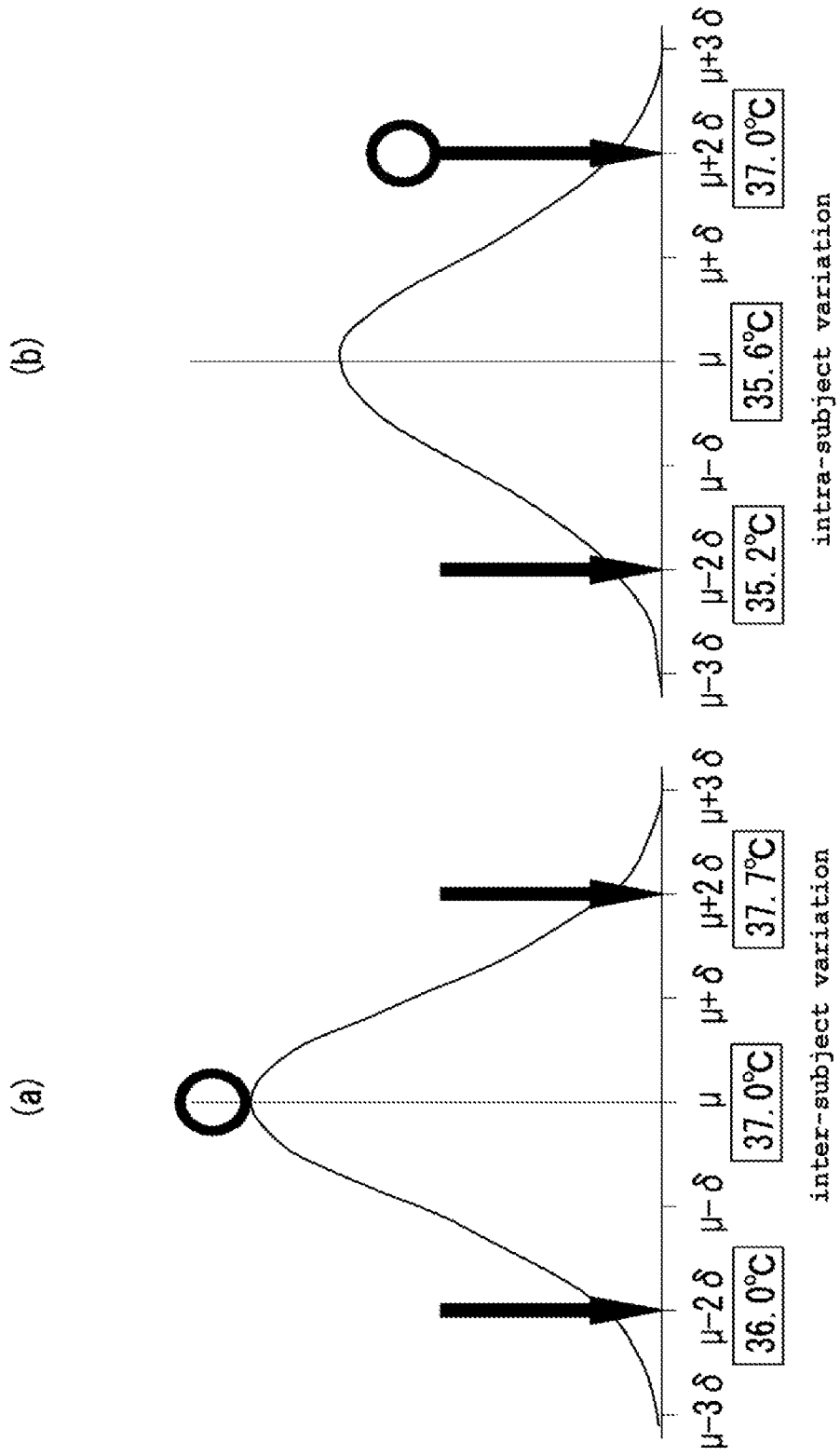
FIG. 11(a) is a normal distribution curve graph created based on vital information of a plurality of subjects.
FIG. 11(b) is a normal distribution curve graph created based on vital information of the same subject.

FIGS. 11(a) and (11b) are normal distribution curve graphs created based on body temperature. In FIGS. 11(a) and 11(b), the horizontal axis represents the probability variable of body temperature, and the vertical axis represents the probability density. Here, (a) is created for a plurality of subjects, and (b) is created for only the same subject. In FIG. 11(a), persons who have several body temperatures or body temperature variation at ordinary times are included, and the mean value µ is 37.0° C. as a mean value for the plurality of subjects and the µ+2σ value is 37.7° C. and µ−2σ value is 36.0° C. However, in FIG. 11(b), the vital information of the same subject is recorded, and the person has distinctive body temperature or body temperature variation at the ordinary times, and thus the mean value µ is 35.6☐ and the µ+2σ value is 37.0☐ and µ−2σ value is 35.2☐.

That is, if the upper limit is set to µ+2σ when the determination of vital information is performed using each distribution, a body temperature of 37.0☐ corresponds to the position of µ (the black circle in FIG. 11(a)) in FIG. 11(a). Meanwhile, a body temperature of 37.0☐ is located at the position of the upper limit µ+2σ (the black circle in FIG. 11(b)) in FIG. 11(b).

That is, 37.0☐ is determined as "an abnormal value" in the determination in FIG. 11(b). In other words, in the determination of the subject in FIG. 11(b), it can be said that the determination standard based on vital information of a plurality of subjects is not used to understand "an abnormal value". The use of vital information of a plurality of persons as a standard is a determination according to "inter-subject variation", which was conventionally performed, and "intra-subject variation" is valid in order to understand the variation of vital information unique to a subject.

In addition, the subject having the mean value or variation in body temperature, shown in FIG. 11(b), does not correspond to a special case. In addition, variations unique to a person are made in the body temperature as well as other vital signs, such as systolic blood pressure, diastolic blood pressure, pulse rate, and respiration rate. In the above example of the body temperature, there are many elderly persons, of which the body temperature changes in the temperature range shown in FIG. 11(b), and thus when the health condition of such elderly persons is determined using a vital sign, "inter-subject variation" is valid.

Hereinafter, an aspect in which, by determining some of the vital information recorded on the vital information recording unit 4 using various types of setting conditions as needed, the vital mean value or the like is calculated or the accuracy of the determination is improved by excluding from the content of the determination standard information 18 will be described.

[5-2. Calculation Considering Rapid Displacement of Vital Information]

In this section, a method whereby vital information showing a rapid displacement is excluded from data when the vital mean value or the like is calculated will be described. In the present method, the vital mean value μ and the vital standard deviation σ for the vital information recorded on the vital information recording unit 4, excluding vital information, of which a displacement from a value of vital information measured on the previous day exceeds a predetermined range, are calculated using the above-described formulas (3) and (4).

The predetermined range of displacement is, for example, a displacement of 0.5☐ or more for the body temperature, 10 times/minute or more for the pulse rate, and 20 mmHg or more for the systolic and diastolic blood pressures. When the vital information recorded on the vital information recording unit 4 is compared with the measurement value on the previous day, the value of the vital information, which varies to exceed a predetermined range of displacement, is excluded from the data calculated in formulas (3) and (4). If the body temperature is 36.8° C. at a certain day of measurement, and 36.3° C. on the previous day, the displacement is 0.5° C. or more, and thus the measurement value of 36.8° C. is excluded. The determination standard can be prepared by excluding the value of vital information, which greatly change for one day, and using the vital information, of which a displacement from the vital information on the previous day is gentle. In addition, the vital mean value and the vital standard deviation described in the present item (5-2) may be the second vital mean value and the second standard deviation in the present description.

In an aspect, a rapid displacement of vital information is excluded from the calculation basis of both the vital mean value and the vital standard deviation, but the present invention is not limited to such an aspect. In an aspect, for example, the vital information showing a rapid displacement is excluded from one of the vital mean value and the vital standard deviation.

[5-3. Calculation Considering Health Inquiry Information]

In the present section, a method whereby if there is any one of the evaluation items determined to be abnormal in the health inquiry information, in consideration of the determination results of health inquiry information, the vital information on that day is excluded from the data when the vital mean value is calculated, will be described. The health inquiry information refers to information on the result wherein at least one health condition inquiry result for a subject is determined to be normal or abnormal for each item. As shown In FIG. 4, the inquiry information 19 for health condition is recorded on the vital information recording unit 4 and a subject can reply to the inquiry information 19 through the display screen 3b and input unit 3a of the tablet terminal 3.

The inquiry information 19 reflects, for example, information about the day of determination and the health condition on the previous day, and there is an inquiry, such as "How is your condition today" or "Did you sleep well yesterday?". Multiple pieces of inquiry information 19 may be set. In addition, the subject selects a reply, such as "good", "bad", "yes", or "no", through the input unit 3a of the tablet terminal 3. According to the results of the selection, the result of "normal" or "abnormal" is connected with and recorded, as the health inquiry information 20, in the vital information recording unit 4. More specifically, as for an inquiry of "How is your condition today?", the reply of "good" leads to a determination of "normal" and the reply of "bad" leads to a determination of "abnormal". If a result of "abnormal" is recorded for any one of the health inquiry information 20, the subject on the day of measurement is assumed to be in a bad condition, and the vital information on the same day of measurement is excluded from the date when the vital mean value or the like is calculated.

As a result, the vital mean value μ and the vital standard deviation σ are calculated using the above-described formulas (3) and (4), except for the vital information on the day when the abnormality is recorded in the health inquiry information 20. Through this setting, the value of the vital information on the day when a subject is assumed to be in poor condition is excluded, and the determination standard can be prepared by using the vital information on the day when a subject is assumed to be in a bad condition.

In addition, the vital mean value and the vital standard deviation described in the present item (5-3) may be the second vital mean value and the second standard deviation in the present description.

Here, the present example shows that the vital information on the day when "abnormal" is recorded in the health inquiry information 20 is excluded from the calculation basis of both the vital mean value and the vital standard deviation, but the present invention is not limited thereto. In an aspect, the vital information on the day when "abnormal" is recorded in the health inquiry information 20 may be excluded for any one of the vital mean value and the vital standard deviation.

[5-4. Calculation Considering Time of Vital Measurement]

In the present section, a method whereby the vital information measured outside the target time for vital measurement is excluded from the data when the vital mean value or the like is calculated will be described. In the present method, the vital mean value μ and the vital standard deviation σ for the vital information recorded on the vital information recording unit 4, excluding the vital information, of which a time difference from target time information 9 recorded on the above-described vital information recording unit 4 exceeds a predetermined range, are calculated using the above-described formulas (3) and (4).

For example, the target time information 9 is the information of the setting time set by a subject, at which daily vital measurement can be easily performed, such as 8:30 in the morning or 18:00 in the evening. In addition, for example, a time period, such as 30 minutes or 1 hour, is selected as a predetermined range of time difference. In the vital information 8 and the re-measurement vital information 13, the vital information measured at the measurement time, which has a time difference from the target time information 9 by a predetermined range or more, is excluded from the data calculated in formulas (3) and (4) above. Through this setting, the vital information outside a range of the predetermined measurement time every day is excluded, and a determination standard can be prepared by using the vital information measured at a determined time and a time around the determined time. In addition, the vital mean value and the vital standard deviation described in the present item (5-4) may be the fourth vital mean value and the fourth standard deviation in the present invention.

Here, the present example shows that the vital information measured at the measurement time, which has a time difference from the time of the target time information 9 by a predetermined range or more, is excluded from the calculation basis of both the vital mean value and the vital standard deviation, but the present invention is not limited thereto In an aspect, the vital information measured at the measurement time, which has a time difference from the time of the target time information 9 by a predetermined range or more, is excluded for any one of the vital mean value and the vital standard deviation.

[5-5. Calculation Considering Temperature Deterioration at the Time of Vital Measurement]

In the present section, a method whereby the vital information measured when the temperature of a place of vital measurement shows a rapid displacement, considering a change in body temperature at the time of vital measurement is excluded from the data when the vital mean value or the like is calculated. In the present method, as for the vital information recorded on the vital information recording unit 4, referring to the time information 11 recorded on the above-described vital information recording unit 4, when, through the temperature information on the day of measurement of certain vital information and the temperature information at the time of vital measurement on the previous day, a displacement between two pieces of temperature information exceeds a predetermined range, the vital mean value μ, and the vital standard deviation σ are calculated from formulas (3) and (4) described above, except for the vital information on the day when the temperature showed a rapid displacement.

For example, the predetermined range of displacement is 2□ or more. As for the vital information recorded on the vital information recording unit 4, when the temperature of a place of viral measurement is compared with the temperature at which vital information is measured on the previous day, and the temperature difference exceeds a predetermined range of displacement in the temperature variation, the vital information on the corresponding day is excluded from the data calculated in formulas (3) and (4) above. Through this setting, the vital information measured when the temperature greatly changes under the environment at the time of vital measurement is excluded, and a determination standard can be prepared by using the vital information measured under the environment with little temperature range.

In addition, the vital mean value and the vital standard deviation described in the present item (5-2) may be examples of the fourth vital mean value and the fourth standard deviation in the present invention. Here, the present aspect shows that the vital information measured when the temperature greatly changes under the environment at the time of vital measurement is excluded from the calculation basis of both the vital mean value and the vital standard deviation, but the present invention is not limited thereto. In an aspect, the vital information measured when the temperature greatly changes under the environment of viral measurement may be excluded from any one of the vital mean value and the vital standard deviation.

The above description shows an aspect in which both of the vital information 8 and the re-measurement vital information 13, which are recorded on the vital information recording unit 4, are included in the calculation basis of the vital mean value, vital standard deviation, and the determination standard information 18 set based thereon, and a plurality of aspects in which the vital information complying with predetermined conditions is excluded from the calculation basis. These can be selected as needed. The respective aspects can be used separately, or in combination. For example, the determination standard information 18 can be set by excluding vital information using two conditions through a combination of the above sections [5-2. Calculation considering abrupt displacement of vital information] and [5-3. Calculation considering health inquiry information]. Also, a combination of all of the aspects can be set. The accuracy of determination can be improved by adopting a plurality of combinations.

[6. Other Determination Methods]

Other determinations by the determination processing unit 6 will be described.

When it is determined that the vital information is an abnormal value, a message saying "Do you want to perform re-measurement?" is displayed on the display screen 3b of the tablet terminal 3 to urge vital re-measurement. In addition, as described above, the posture information 10 recorded on the vital information recording unit 4 is displayed, and a message saying "Have you perform vital measurement in the right posture?" is displayed. A message saying "Did you conduct vital measurement at a set measurement time?" may also be displayed.

As such, a subject who inputs the vital information is urged to call attention, and then a reply to the effect of re-measurement of vital information is performed through the input unit 3a of the tablet terminal 3 by the subject himself or herself. Vital information is again measured, and the result information can be recorded on the vital information recording unit 4. This becomes re-measurement vital information 13.

The re-measurement vital information 13 is used as a calculation basis of the vital mean value, vital standard deviation, and determination standard information 13, subsequently. When each piece of vital information is displayed on the display screen 3b of the tablet terminal 3, characters indicating three pattern vital information, such as usual vital information recorded without re-measurement, vital information as an object of re-measurement, and re-measurement vital information, are displayed in different colors.

In another aspect in which the determination processing unit 4 determines the vital information as "an abnormal value", the vital information is determined as "an abnormal value" if there is any doubt of catecholamine release from the results of vital information of the subject. The catecholamine release is the release of catecholamine (a kind of adrenocortical hormones by physical stress. Cerebrovascular diseases and cardiac diseases are one of the pathological conditions caused by catecholamine release, and as a method of detecting these, a determination standard for suspected catecholamine release may be prepared.

The physiological sign of suspected catecholamine release is "an acute increase in blood pressure accompanied by a large pulse pressure", and the determination conditions involved in vital information are accompanied by an increase in blood pressure (displacement of blood pressure) for vital information of systolic blood pressure and diastolic blood pressure. When a value of vital information (blood pressure) satisfying formula (5) below is confirmed, the possibility of the onset is suspected.

Large pulse pressure≥Systolic blood pressure/2   Formula (5)

The large pulse is a value induced from "maximal blood pressure (systolic blood pressure)−minimal blood pressure (diastolic blood pressure)". The "systolic blood pressure/2" is the systolic blood pressure (minimal blood pressure) divided by 2.

If the vital information is accompanied by an increase in blood pressure and the vital information suitable for formula (5) above is obtained, it may indicate the possibility of catecholamine release.

As such, a condition in which catecholamine release is suspected is set as one of the determination standard information 18, and can be determined as "an abnormal value" by the determination processing unit 6. As described above, when there has been a determination of "an abnormal value", the re-measurement of vital information can be urged.

As another determination method by the determination processing unit 6, a method whereby it is determined that "there is a possibility of abnormality" when the vital mean value satisfies a predetermined condition will be described.

Here, when, through a comparison between the vital mean value for the last 7 days and the vital mean value for the last 30 days using the vital information recorded on the vital information recording unit 4, a difference between two vital mean values exceeds a predetermined range, the determination processing unit 6 determines that "there is a possibility of abnormality".

The predetermined displacement in the difference between the two mean values may be, for example, set as a value of 0.5σ or more based on the vital standard deviation σ on the day of determination. The vital mean values for the last 7 days from the day of determination and for the last 30 days from the day of determination are expected to be about the same as usual, even though the intra-subject variation is included in the vital information of the subject. However, if the difference between the two vital mean values is 0.5σ or more, there is a large fluctuation in the vital mean value, from which the subject may not be determined as having "an abnormal value", but it is determined that "there is a possibility of abnormality", which is used as an indicator that there is a possibility that the condition will deteriorate.

The vital mean value for the last 7 days and the vital mean value for the last 30 days are examples of the "recent vital mean value" and "contrast vital mean value" in the present claims.

As described above, the determination processing unit 6 determines that "there is a possibility of abnormality", indicating the deterioration of condition, through comparison between the two vital mean values within a predetermined period range, thereby calling the attention of the subject or contributing to preventive medicine. The number of days, such as the last 7 days and the last 30 days, are not necessarily limited thereto. The vital information on the day of determination may be included or may not be included in the calculation basis of the vital mean value, but the vital information on the day of determination is preferably included therein since the fluctuation or non-fluctuation of the vital mean value at the time of determination can be confirmed by including the vital information on the day of determination therein.

[7. Creation of Display Information]

The health condition determination apparatus 1 employing the present invention can display a content of the vital information of the subject as a normal distribution curve. In addition, the health condition determination apparatus 1 can display the vital information of the subject as a body temperature table. Both are examples of the display manner of the vital information of the subject, but these are display forms that facilitate the visual confirmation of the intra-subject variation of the vital information of the subject. These pieces of information can be confirmed not only on the display screen 3b of the tablet terminal 3 but also through an external server or the like.

[8. Determination of Measurement Accuracy by Presence or Absence of Normal Distribution and Determination of Abnormal Value]

The determination of measurement accuracy by the presence or absence of a normal distribution and the determination of an abnormal value will be described with reference to FIGS. 12 and 13. The health condition determination apparatus 1 employing the present invention can use the Q-Q plot as a mean for investigating whether or not the measured vital information is suited for a normal distribution. For example, the vital standard deviation of the subject is plotted by taking a vital standard deviation value on the horizontal axis and a percent point value of the standard normal distribution corresponding to a cumulative probability of the standard deviation on the vertical axis. If each plot is located on the straight line, this visually confirms that the obtained vital information is normally distributed.

Figure 14:
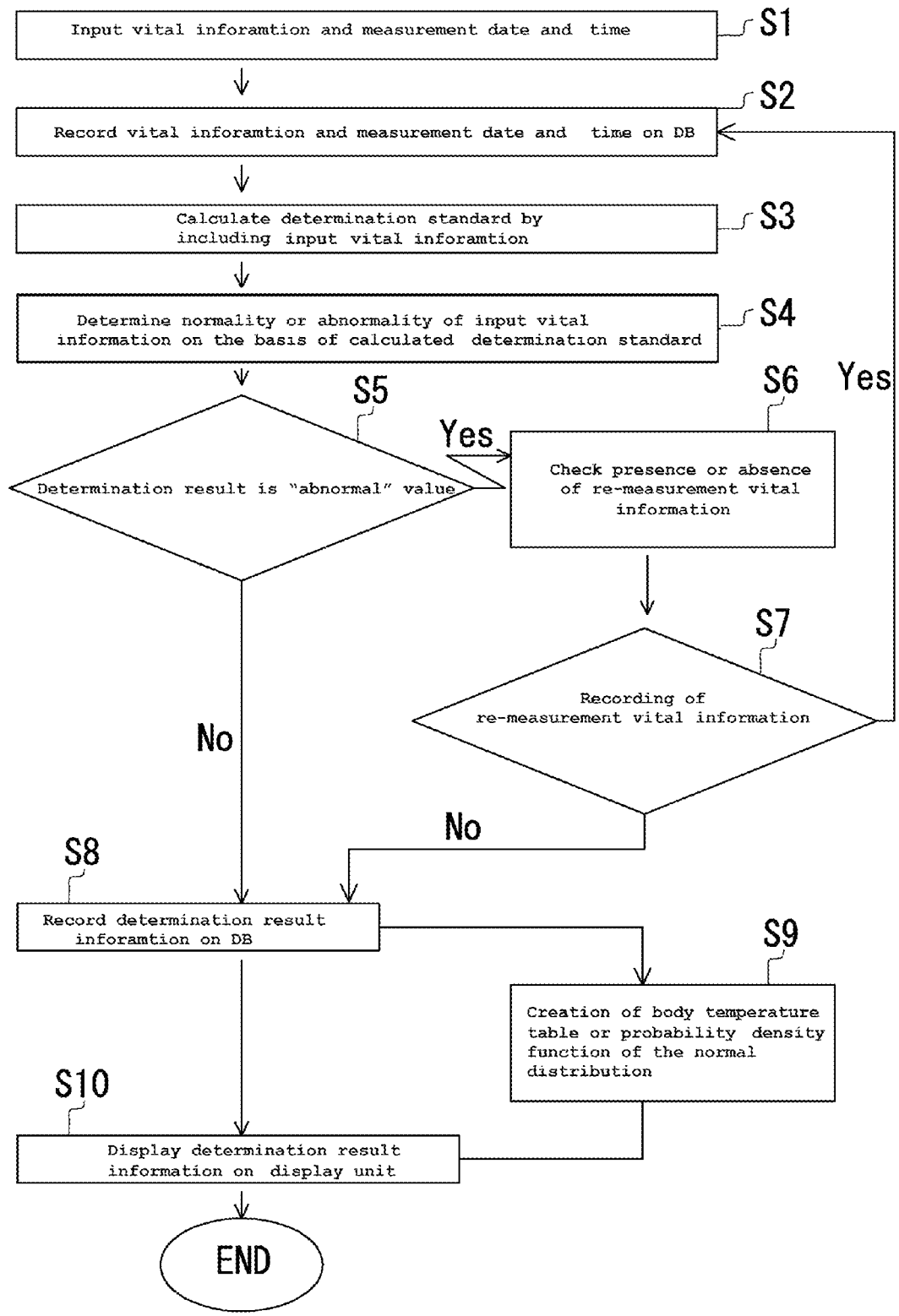
FIG. 14 is a flowchart showing an information processing flow of the input of vital information, the determination of normality or abnormality, and then the display of resulting information.

For example, FIG. 12 (*a*) is a graph showing a QQ plot of the standard deviation of body temperature for a predetermined period in a certain subject. In FIGS. 12 to 14, each horizontal axis indicates an accumulative probability of a certain measurement value of a vital sign of the subject, and each vertical axis indicates a percent point of the standard normal distribution corresponding to an accumulative probability of a certain measurement value. As shown in FIG. 12(*a*), most of the plots in the standard deviation of the body temperature of the subject are located on the straight line, and thus it can be confirmed that the body temperature is normally distributed. Similarly, FIG. 12(*b*) is also a graph showing a Q-Q plot of the standard deviation of the systolic blood pressure. Here, most of the plots are located on the straight line, and thus it can be confirmed that the body temperature is normally distributed.

Meanwhile, in the Q-Q plot of the standard deviation of the respiration rate shown in FIG. 13(*a*), the plots located in the region around 1.0 as a value of the horizontal axis and 2.5 or greater as a value of the vertical axis are not located on the straight line but largely deviate therefrom. It can be confirmed from these results that the respiration rate obtained from the subject is not normally distributed. In the Q-Q plot of the standard deviation of the oxygen concentration (oxygen saturation) shown in FIG. 13(*b*), one point of the plot located near 3.5 as a value of on the horizontal axis is not located on the straight line but largely deviates therefrom. This case shows a behavior close to the normal distribution, but there may be a possibility that the vital measurement of the day, deviating from the straight line, was not correct. The value of a percent point of the standard normal distribution, corresponding to a cumulative probability of the standard deviation, which is the value of the vertical axis of the Q-Q plot, can be calculated using the already known function of software or the like, and in conjunction with the functions, Q-Q plots may be created each time. As described above, the accuracy of the vital measurement every day can be confirmed by checking, through the Q-Q plots, whether or not the vital information is normally distributed. As for an additional function, when there is a value out of a predetermined range from the straight line connecting plots after the Q-Q plot is created, a function of displaying such a meaning in any form may also be adopted, and it can be easily confirmed that there is a value deviating from the normal distribution, resulting therefrom.

Next, a series of information processing flows in the software employing the present invention will be described with reference to FIG. 14.

FIG. 14 shows an information processing flow from the input of vital information to the determination of normality or abnormality, and then the display of resulting information.

First, a value of a vital sign of a subject is measured by each measurement instrument, and information of the measurement value and the measurement date and time is input (S1). The input information is recorded as vital information of the subject in the vital information recording unit 4 (DB).

The calculation unit 2 functions as the standard calculation unit 5, including the vital information, as an object of determination, recorded on the vital information recording unit, to calculate a determination standard (S3). Here, the vital mean value and the vital standard deviation are calculated, based on which the determination standard (e.g., an upper limit value or a lower limit value) under the set conditions is created. That is, the determination standard is calculated each time when the determination is made. As described above, some of the vital information may be excluded from the calculation basis of the vital mean value or the vital standard deviation when satisfying predetermined conditions.

Figure 15:
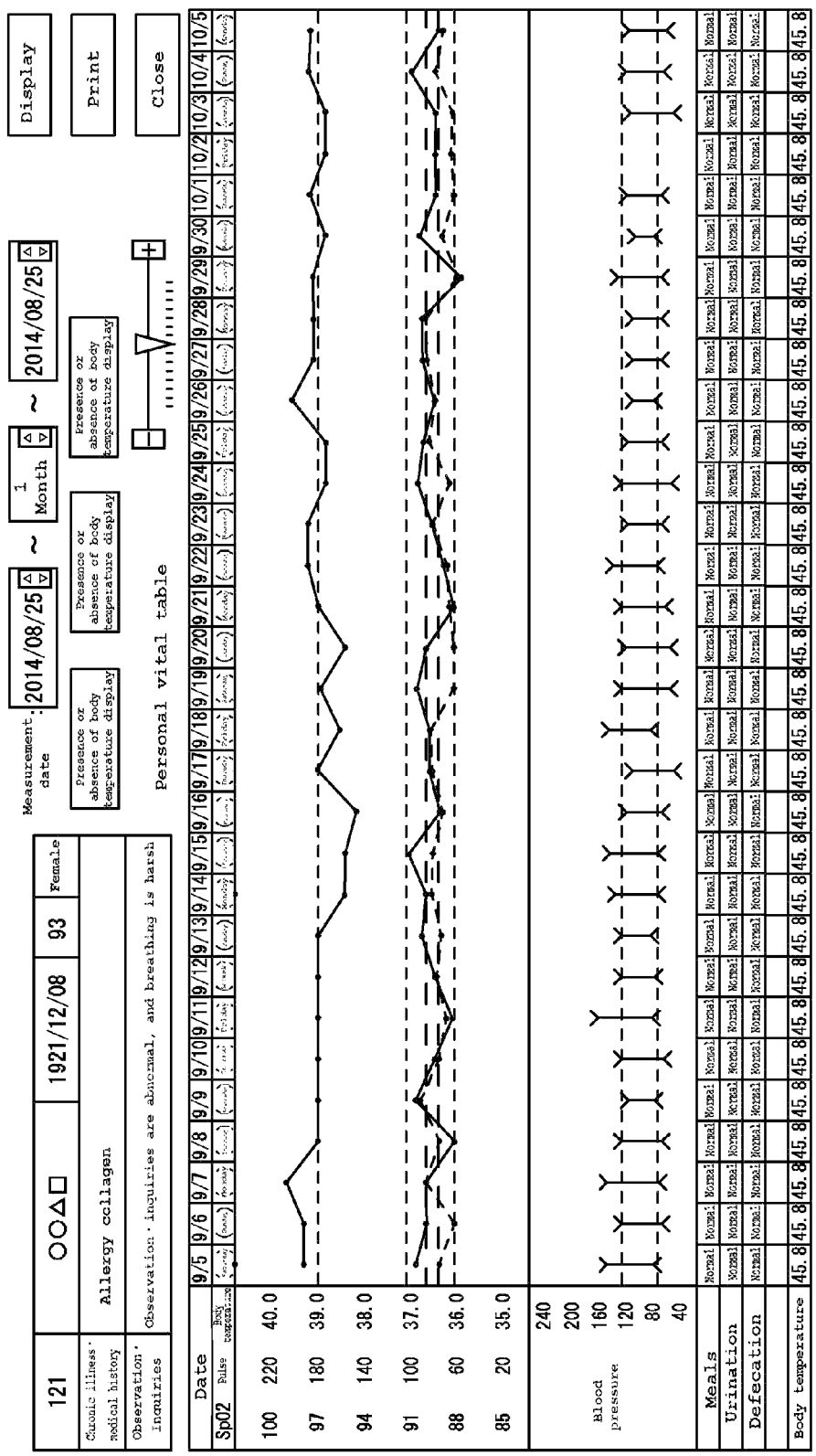
FIG. 15 is a schematic diagram showing an example of a body temperature table.

Subsequently, it is determined whether or not the input vital information as an object of determination is an abnormal value based on the determination standard (S4). As for the vital information not determined as "an abnormal value" as a result of determination, the determination result information is recorded on the vital information recording unit 4 (DB) and the information of the determination result is displayed on the display screen 3b (S10). A body temperature table (see FIG. 15) or a probability density function of the normal distribution (a graph of the normal distribution curve), obtained by plotting a change over time of the value of vital sign based on the vital information of the subject, is created as display information (S9), and the information thereof can also be confirmed on the display screen 3b.

Subsequently, it is determined whether or not the input vital information as an object of determination is an abnormal value based on the determination standard (S4). if it is determined that "it is an abnormal value" as a result of determination, for example, a message saying "Do you want to perform re-measurement?" or indicating calling attention of the posture at the time of acquiring vital information is displayed on the display screen 3b, and then the subject is asked whether or not there is re-measurement vital information (S6).

Here, if the subject selects "There is no re-measurement vital information", the determination result information indicating a determination of abnormality is recorded on the vital information recording unit 4 (DB), and the information of the determination result is displayed on the display screen 3b (S10). In addition, a body temperature table (see FIG. 15) or a probability density function of the normal distribution (a graph of the normal distribution curve) is created as display information (S9), and the information thereof can also be confirmed on the display screen 3b.

If the subject selects "There is re-measurement vital information", the subject is asked to input the re-measurement value of the vital sign and the measurement data and time thereof, and the input re-measurement vital information is recorded as re-measurement vital information in the vital information recording unit 4 (DB) (S2). Thereafter, the calculation of the determination standard (S3) and the determination on abnormality (S4) are performed. If it a determination of an abnormal value is not made, the determination result information is recorded on the vital information recording unit 4 (DB) (S8). If a determination of an abnormal value is made, the step of verifying whether or not there is re-measurement vital information (S6) may be performed, or the recording of the determination result information (S8) may be performed since the determination result information corresponds to the second determination result.

The subject confirms the determination result information on the display screen 3b, and thus a series of information processing steps is completed. Through the above flows, the software employing the present invention determines the health condition from the vital information.

Figure 16:
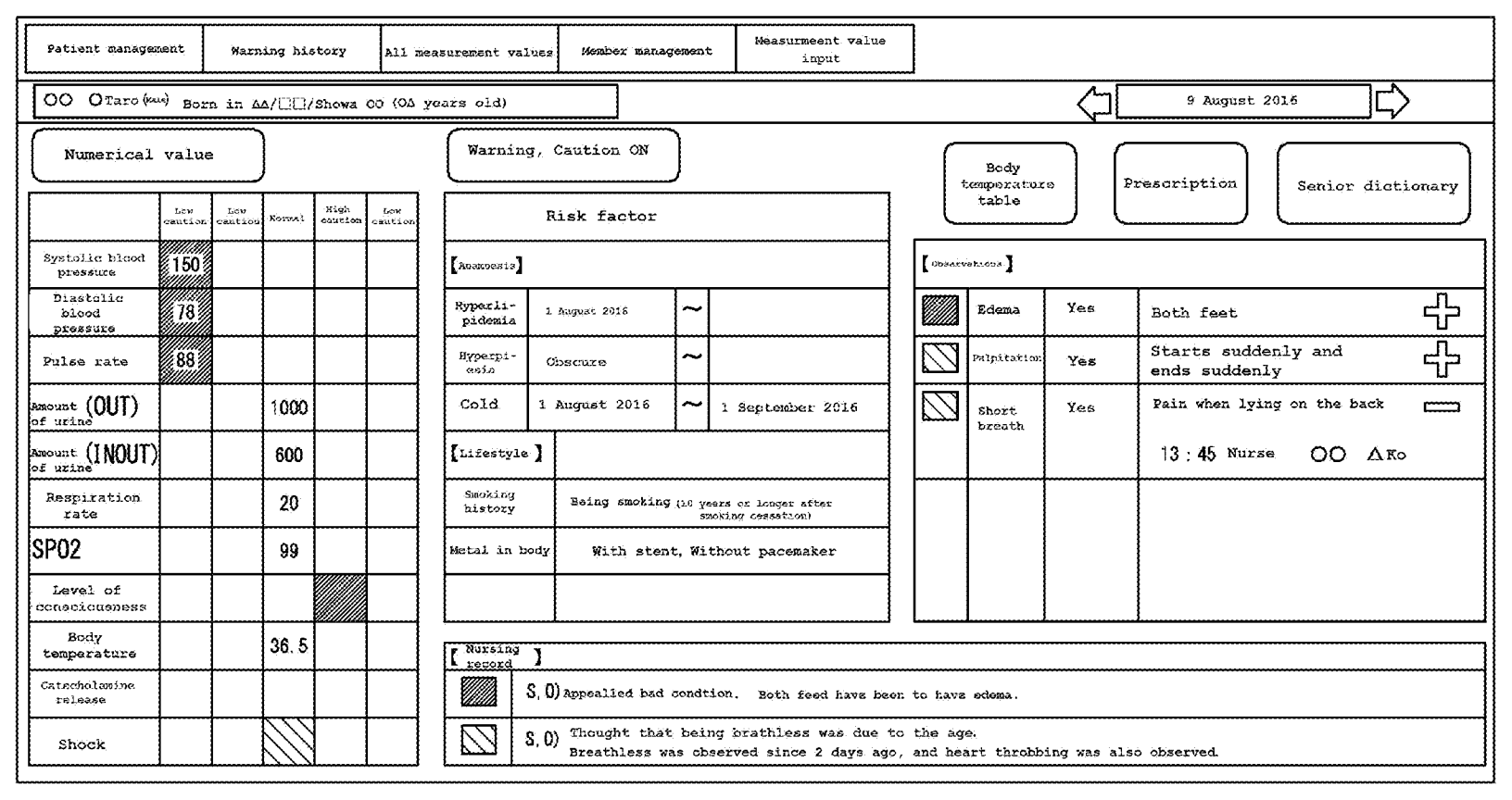

The determination result information may be displayed by not only a result of the presence or absence of abnormality, a body temperature table (see FIG. 15), and a probability density function of the normal distribution, but also a combination with a pathological condition panel of the subject (see FIG. 16). The pathological condition panel shown in FIG. 16 includes information of, in addition to the values of vital signs value, risk factors (past medical history and lifestyle) related to diseases, nursing records, and observation contents, and more particularly, may show health condition of the subject, especially, information related to diseases, together.

[Embodiment in Determination of Heatstroke]

The software employing the present invention can be used in the determination of heatstroke.

Specifically, as for, for example, a worker who performs work in an outdoor environment, as a subject, it is determined whether or not the vital information at the time of work, monitored and obtained at predetermined intervals, is abnormal.

Figure 7:
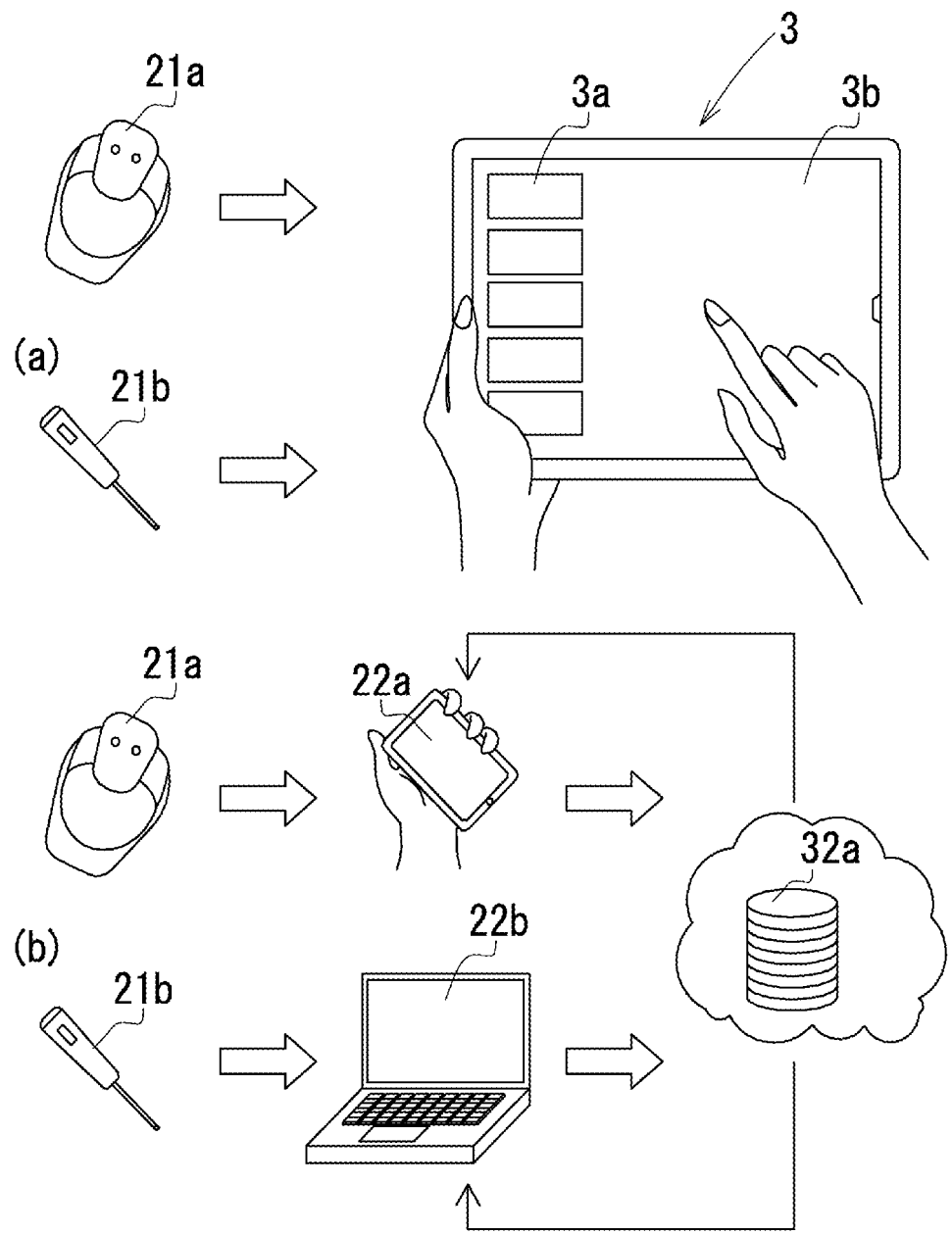
FIG. 7(a) is a schematic diagram showing an example of an apparatus used when a software employing the present invention is functioned.
FIG. 7(b) is a schematic diagram showing another example of the apparatus.

In the present embodiment, the subject wears a wearable type vital measuring instrument 21a (see FIG. 7 (a)) on the arm, and the obtained vital information is transmitted to a management terminal through a smartphone terminal 22a (see FIG. 7(b)) carried by the subject.

Various vital signs at the comfortable condition before work (standard vital information) and, for example, every hour from the work start point (monitoring vital information) are measured by the vital measurement instrument 21a worn on the arm of the worker. The vital signs are mainly a body temperature, a pulse rate, a diastolic blood pressure, a systolic blood pressure, and a respiration rate. The obtained vital information is measurement information, and automatically transmitted, together with day of measurement and time information, to the smartphone terminal 22a. Here, the measurement time is not limited to one hour, and thus the setting thereof can be appropriately changed.

The smartphone terminal 22a receiving the measurement information from the vital measuring instrument 21a further transmits the information to the management terminal. The management terminal accesses the information management server 32a (see FIG. 2), with the measurement information, which is then recorded on the vital information record section 4a. The measurement information is also recorded on the management terminal. Here, the software of the present invention is introduced into the information management server 32a to perform the recording of information, the calculation of a determination standard, and the determination of normality or abnormality.

The operation unit 2a of the information management server 32a functions as the standard calculation unit 5a to calculate the vital mean value and vital standard deviation of the subject and calculates the determination standard base on the calculated vital mean value and vital standard deviation. The calculation of the vital mean value and the vital standard deviation may be performed by using either or both of the standard vital information and the monitoring vital information.

The operation unit 2a of the information management server 32a functions as the standard calculation unit 5a, and determines the normality or abnormality of the vital information transmitted from the smartphone terminal 22a and recorded, by using the determination standard calculated by the standard calculation unit 5a. The determination result is transmitted from the information management server 32a to the smartphone terminal 22a, and the worker can confirm the determination result on the terminal screen.

When it is determined that the vital information is an abnormal value, the smartphone terminal 22a is notified of a situation by a warning sound or the like to stop the work or notify the work manager, so that the worker check his or her condition before causing abnormal condition, and thus can prevent accidents or the like in advance.

The following exemplifies a determination that the monitoring vital information of the body temperature in the present embodiment is abnormal.

Figure 17:
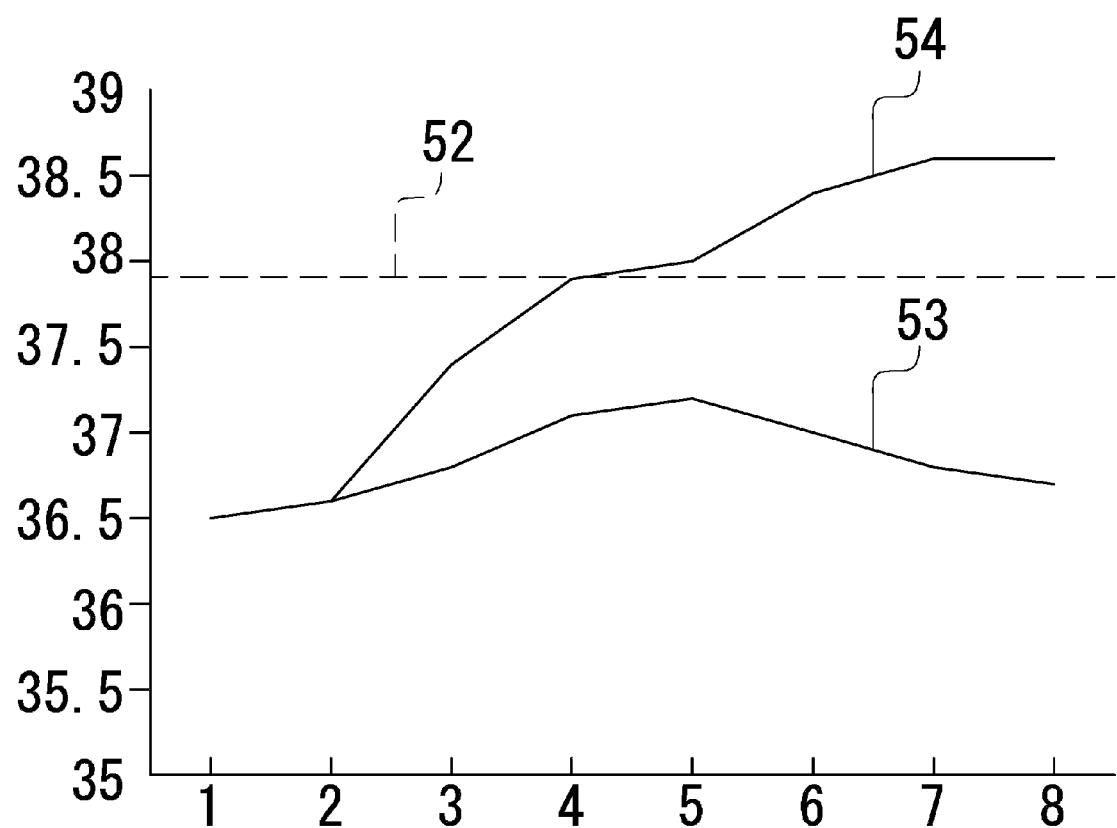
FIG. 17 is a graph showing the change in body temperature over time when a determination of heatstroke is made in the software employing the present invention.

FIG. 17 is a graph showing an example of a variation in monitoring body temperature of a subject during a predetermined time on a certain working day.

In FIG. 17, the vertical axis represents indicates the value of the monitoring body temperature (□) and the horizontal axis represents the elapsed time (hours) from the start of work. It is also assumed that the line denoted by reference numeral 52 is the upper limit (e.g., $\mu+2\sigma$) of the determination standard for making a determination of abnormality when each monitoring body temperature is measured. In addition, the two types of curves indicate the results not serving as an object of determination of abnormality (reference numeral 53) and the results serving as an object of abnormality (reference numeral 54), respectively, in the monitoring body temperature. The values are actually not constant like the line indicated by reference numeral 52 since the determination standard is calculated each time when each monitoring body temperature is recorded. However, for convenience, the values are assumed to be constant in order to explain the presence or absence of a determination of abnormality.

As shown in FIG. 17, all the monitoring body temperature data on the curve indicated by reference numeral 53 are lower than the upper limit of the determination standard, and a determination is not made that the vital information of the body temperature is an abnormal value. The monitoring body temperature data after 4 hours to 8 hours from the start of the measurement on the curve indicated by reference numeral 54 are equal to o higher than the upper limit of the determination standard, and therefore, a determination is made that the vital information is an abnormal value after each measurement of monitoring vital information.

As described above, the normality or abnormality of the vital information can be determined by measuring the monitoring body temperature every predetermined time from the measurement start time point of the body temperature. Similarly, the determination of normality or abnormality can be made for vital signs, such as pulse rate, diastolic blood pressure, systolic blood pressure, and respiratory rate, in addition to the body temperature shown in FIG. 17.

INDUSTRIAL APPLICABILITY

Hereinafter, additional application examples of the health condition determination apparatus employing the present invention will be described.

[Conjunction with Electronic Charts or Medical Systems]

The health condition determination apparatus employing the present invention may be considered to be in conjunction with electronic charts introduced into hospitals. Since the electronic chart has information of patients in a hospital at which the electronic chart is installed, more detailed information of a subject of situations of underlying diseases, past medical history, medication record, progress observation, and the like, can be used by conjunction of the electronic chart with the information managed by the software employing the present invention.

Furthermore, the diagnostic progress information by doctors can be confirmed, thereby improving the accuracy of determination of the health condition and increasing the convenience as a diagnostic support tool. In addition, the diagnostic results or examination results by hospitals are added to the information of a subject, thereby increasing the amount of information of a subject, leading to a determination with higher accuracy. Furthermore, the electronic chart becomes more useful as a diagnostic support tool.

The health condition determination apparatus employing the present invention may be combined with a system for remote image diagnosis. For example, a device capable of acquiring image information, such as a camera, may be connected to the health condition determination apparatus, and thus the image information of the subject may be transmitted to a hospital, thereby enabling remote diagnosis. At that time, the information of the body temperature table of the subject is also transmitted to a terminal of the hospital, so that a doctor can diagnose at a remote location while checking the abnormality of the vital values of the subject.

In the health condition determination apparatus employing the present invention, variations of a plurality of operating boards may be considered according to the level of a user. For example, the health condition determination apparatus employing the present invention becomes a diagnosis support too in the diagnosis by a doctor in a hospital if it is in a state of conjunction with the electronic chart as described above. Here, the information managed by the diagnostic apparatus contributes to an increase in the diagnostic level of a doctor since the hospital diagnostic information on each day is accumulated.

In addition, a particular nurse is allowed to carry with a tablet terminal having functions of the present invention in a hospital, so that the nurse use the tablet terminal as a support tool when performing a diagnosis instead of a doctor. Furthermore, the nurse with the tablet terminal is helpful when visiting and nursing homes for elderly people residing at home or in the facility.

Furthermore, when a staff of a nursing facility or like uses the tablet, the staff can improve the diagnostic level for a specific subject by accumulating information specialized for a resident.

[Application to Disease Prevention Technology]

The health condition determination apparatus employing the present invention can be used for prevention techniques of representative diseases, of the onset can be predicted by fluctuations of vital signs, such as brain disease, pneumonia, heart failure, and dehydration. Each of the above-mentioned diseases often has a vital sign fluctuation unique to each disease at the time of onset, and the vital sign fluctuation unique to each disease is set as a determination condition, leading to the prevention of the onset.

[Utilization to Personal Health Record (PHR) and Medical Big Data]

In recent years, due to the remarkable development of information and communication technology called information and communication technology (ICT) and the rise of an information terminal, such as a smart phone, an Internet communication environment using wireless LAN, and inexpensive and high-capacity database, such as a cloud serve, massive data can be transmitted and received at a high speed. As a result, all the data, so-called big data, are gathered in the world and services for various purposes are performed by using necessary data.

The Ministry of Health, Labor and Welfare of Japan intends to realize the "regional comprehensive care system" by 2025, in which medical care, nursing, prevention, housing, and daily life support are comprehensively secured, in order to support elderly people throughout the region in a super-aged society. However, most of the underlying medical information is disconnected at each establishment.

For example, information sharing among medical institutions is still performed by using facsimile, or frequently, there is no continuity of health data between facilities, and these aspects have been shown throughout the ages, considering the era called the Fourth Industrial Revolution. Medical and information alliance networks are attempted in more than 170 locations nationwide, but cannot cover the whole area and population in the country nationwide, and have problems, such as low operation costs and utilization rates, and thus the networks are not integrated into a common platform.

Therefore, the Ministry of Health, Labor and Welfare of Japan is considering the PHR scheme "having a purpose that every citizen manages health, medical care, and nursing information throughout one's lifetime in a time series manner and utilizes the information by oneself, thereby receiving high-quality services conforming to the health condition of oneself" (in the "Discussion about the nature of medical ICT in the cloud era" by the Ministry of Internal Affairs and Communications and Ministry of Health, Labor and Welfare). PHR is an abbreviation of Personal Health Records. PHR is a tool that allows a subject to collect or preserve medical information and health information about oneself throughout one's lifetime, and to utilize the same.

According to the PHR, "Since the comparison with past information as well as recent information is needed, a subject can manage the information during one's lifetime and utilize the information in a desired service at a desired time", and if this PHR scheme is realized, this tool, without an integration into a platform, can be variously operated by alliance with medical care, nursing, health, and personal information, such as "electronization of nursing and prevention notebook" or "electronization of health checkup information and unitary management of vital data and living-related information in municipalities or workplaces".

As for not only the "PHR scheme", by which in order for respective provincial governments to cooperate to create an environment facilitating the utilization of big data, the form of data (API or the like) is unified to allow easy withdraw of necessary data, but also the "medical ID" scheme, which makes it easy to identify and maintain personal data, called my medical number, "Amendment of Personal Information Protection Act" is designed to utilize anonymized information without personal permission, for development or therapy.

These schemes illustrate vital data as follows. "After anonymizing health, medical, and nursing information of a subject, the analysis and utilization thereof as big data, that is, the secondary use should also be considered as an important factor in reviewing the sustainability of PHR service. Especially, various devices and services regarding vital data currently exist in the market, but when vital data are utilized in integration with into PHR, the secondary use should be considered for the purpose of analyzing the effect of health care, and it is desirable to unify API with data granularity and PHR collecting platform."

Thereafter, the health condition determination apparatus (or the health condition determination method) employing the present invention may be in conjunction with the PKR scheme. The utilization of vital data through the incorporation into the present apparatus is largely different from an existing technique in that, when health care is performed, the comparison with general data is not conducted, but "tailor-made diagnosis", which is tailored to characteristics of each individual, so-called "individualized medicine" is used. Furthermore, the interpretation of medical big data opens the way of preventive medicine, and "artificial intelligence" becomes helpful for its support. In the future, the health condition determination apparatus employing the present invention will greatly contribute to the realization of the PHR scheme.

[Education Software for Doctors and Nurses]

Furthermore, the health condition determination apparatus of the present invention can be used as a training tool for a healthcare worker. The pathological discrimination flow chart database is combined with the present invention, and based on the information thereof, educational software combining questionnaires and answers can be created. In addition, the scores of a plurality of healthcare workers using educational software are recorded, and ranked, so that doctor and nurse assessment sheets can be created.

[Reference Tool when Nurse Prescribes Medicines]

Furthermore, the health condition determination apparatus of the present invention can be used as a reference when a nurse prescribes medicines. For example, the medication history of a subject is recorded in the personal information of the subject. As a result, the data of "What medicines have been prescribed for symptoms?" are accumulated, and a pharmacist can utilize the data as reference information at the time of medication. Depending on the type of medicine, the health condition determination apparatus of the present invention can be developed for medication without going through a pharmacist. The confirmation of medication history by a pharmacist can be easily performed.

[Medication Management and Delivery Service]

Furthermore, the information of medication history is linked with the delivery service, so that the regularly needed medicines of a subject can be automatically delivered to the subject in times of need.

[Link to Medical Examination Data at Work or School]

The health condition determination apparatus of the present invention can record and utilize regular health examination information at work or school. Here, the acquisition period of the vital information is empty, and thus the determinations of caution, warning, and abnormality are appropriately set. These help the health care of a subject. In addition, these become a mean for obtaining vast clinical data. Furthermore, comprehensive health care for a subject can be achieved by linking with the information of health examination conducted by public agencies.

[Local Health Care at Remote Sites]

The health condition determination apparatus of the present invention can be used in the local health care at remote sites. For example, the health condition determination apparatus of the present invention may be installed in the countries during overseas business trips, ships that are engaged in deep-sea fishing, and the overseas dispatches of Self-Defense Forces, and the like. As a result, the health care of a subject can be attained even in a country where the medical level is low, a place where a medical facility does not exist, and the like. In addition, the diagnosis by a doctor can be performed by combining with the above-described remote diagnosis.

[Checking Disease Occurrence by Region]

The health condition determination apparatus of the present invention can contribute to preventive medical treatment of local medical care by linking with the information of disease occurrence by region. For example, the health condition determination apparatus can contribute to preventive measures in the regions using the health condition determination apparatus by linking with the information on epidemic influenza. In addition, the information on a subject in the epidemic area can be utilized as clinical data.

[Detection of Air Environment]

The health condition determination apparatus of the present invention can be combined with the air environment detection mechanism. The air environment detection mechanism detects the concentration of formaldehyde or PM2.5 to determine the air pollution degree of the area from the concentration, and then urges an apparatus user to call attention. In addition, the health condition determination apparatus of the present invention can also be utilized as an information acquisition tool for calling the attention of residents in target areas or the improvement of environment.

[Utilization to Adjustment of Indoor Environment]

The health condition determination apparatus of the present invention can be utilized for a healthcare home, which can adjust the room temperature and humidity by an air conditioning device, based on the information recorded in the health condition determination device of the present invention. The environment can be controlled to the room temperature or humidity suitable for a subject, of which a value of a vital sign is determined to be an abnormal value, or to an appropriate set temperature at which a healthy state is easy to maintain.

[Nursing Record Software and Nursing Billing Software]

The health condition determination apparatus employing the present invention may be in conjunction with nursing record software or nursing billing software. The information management unit manages the information of nursing record input into the nursing record software, and thus accumulates data of "What type of nursing is appropriate for symptom?". As a result, a uniform service can be provided to a subject of nursing irrespective of the function level of a nurse. In another aspect, the health condition determination apparatus employing the present invention may be in conjunction with the nursing record software.

The health condition determination apparatus employing the present invention can be used as a support tool for calculating nursing cost when being linked with the nursing billing software. As a result, the costs incurred for the provided nursing content can be easily grasped, leading to the improvement in work efficiency.

[Health Check of Nursing Staff]

The health condition determination apparatus employing the present invention can be utilized for checking the health condition of a nursing staff. Health care is performed by measuring the vital information of the nursing staff and sending the same to the health condition determination apparatus. As a result, the working environment of the nursing field can be improved.

[Monitoring Function]

The health condition determination apparatus employing the present invention, when being in conjunction with a monitoring system for an elderly person in a nursing facility or living single, may sent a notification to a monitor (for example, family) if the vital value is determined to be abnormal or a subject shows an abnormal motion. For example, a person monitoring sensor is installed in the house, and thus, when a owner does not move for a predetermined time in the bathroom, a notification is automatically sent to a security company or family. At that time, the record of the vital information of the monitor may be simultaneously transmitted as data.

[Diet and Condition Management]

The health condition determination apparatus employing the present invention can also be utilized as an apparatus for supporting diet or condition management of a user. For example, an advice for weight loss may be displayed based on the vital information and the information of meal calorie intake. In addition, the health condition determination apparatus employing the present invention can provide a plurality of weight loss programs by cooperating with a facility, such as a training gym.

[Application to Wearable Device]

The health condition determination apparatus of the present invention can be in conjunction with a wearable device. In recent years, a small wearable device, which can be mounted on the body, has been developed, and therefore, various types of vital information, such as body temperature, pulse rate, systolic blood pressure, and diastolic blood pressure, can be obtained in real time using these devices. The health condition determination apparatus of the present invention can be combined with a wearable device as a vital information acquisition unit or a determination result display unit, thereby greatly widening the application range of the apparatus. In addition, the health condition determination apparatus of the present invention can be utilized as a device for self-management for self-management of condition.

[Utilization of Application Software]

The function of the health condition determination apparatus of the present invention is provided as an application software, and can be used through a mobile terminal or a tablet terminal. As a result, the function of the present apparatus can be easily utilized, thereby improving convenience. Furthermore, the present apparatus contributes to improvement of the penetration rate, so that a wider range of clinical data can be obtained.

[Shopping Support Software]

The information recorded in the health condition determination apparatus of the present invention can be in conjunction with a product sale website on the Internet or a software supporting the purchase of products. The reference information at the time of product purchase is obtained by imparting a function of recommending foods or health machines fitting the health condition of a user.

[Animal Health Care]

The health condition determination apparatus of the present invention can be used for an animal as a subject. The health condition determination apparatus can contribute to the health care of not only humans but also pets and animals in the zoo, and the protection of wild animals. Furthermore, medically and academically useful information is obtained by accumulating clinical data and diagnostic information of animals,

[Installation in Vehicle]

The health condition determination apparatus of the present invention can be installed in a vehicle. For example, a vital measurement instrument (for example, a thermometer, a pulse system, a respiration rate sensor, or the like) is installed in the seat of a driver, and then when the condition of the driver is suspected to be defective, the drive is urged to call attention. Furthermore, the health condition determination apparatus of the present invention can check drunk driving by combining with an alcohol detector.

As described above, the health condition determination apparatus of the present invention can grasp a different intra-subject variation for a different subject with high accuracy by reflecting a vital sign considering an individual difference of the subject or daily condition of the subject, and can contribute to health management of the subject or the provision of medicine suitable for each personality.

Furthermore, the health condition determination method of the present invention can grasp a different intra-subject variation for a different subject with high accuracy by reflecting a vital sign considering an individual difference of the subject or daily condition of the subject, and can contribute to health management of the subject or the provision of medical care fitted for each personality.

EXPLANATION OF REFERENCE NUMERALS 1. health condition determination apparatus
   1a software
2 operation unit
   2a operation unit
3 tablet terminal
   3a input unit (of tablet terminal)
   3b display screen (of tablet terminal)
   3c information transmission and reception unit (of tablet terminal)
4 vital information recording unit
   4a vital information recording unit
5 standard calculation unit
   5a standard calculation unit
6 determination processing unit
   6a determination processing unit
7 personal information
8 vital information
9 target time information
10 posture information
11 temperature information
12 determination result information
13 re-measurement vital information
14 mean value calculation unit
15 standard deviation calculation unit
16 normal distribution calculation unit
17 determination standard setting unit
18 determination standard information
19 inquiry information
20 health inquiry information
21a vital measurement instrument
21b thermometer
22a smartphone
22b personal computer terminal (PC terminal)
23 information input unit
24 information recording unit
   24a information recording unit
30a internet
32a information management server
32b software
32c software
32d software
50a user terminal
50b external terminal
60a user terminal
60b external terminal
70b management terminal

The invention claimed is:

1. A system for determining a health condition of a subject, based on vital information corresponding to a measured value of a vital sign, wherein the system allows an information processing device to function as a unit, the system comprising:
   one or more memory mediums;
   one or more processors coupled to one or more memory mediums;
   an information input unit configured to receive vital information following a normal distribution measured from the subject and a measurement date and time information;
   an information recording unit configured to allow the vital information and the measurement date and time information to be recorded thereon;
   a standard calculation unit configured to calculate mean $\mu$ and/or standard deviation $\sigma$ of all or some of multiple pieces of vital information recorded on the information recording unit; and
   a determination unit configured to determine if an input predetermined vital information is an abnormal value, based on a predetermined numerical range set from the mean $\mu$ and/or the standard deviation $\sigma$ wherein the predetermined numerical range being set is based on a normal distribution having at least the mean $\mu$ as a peak;
   wherein the input predetermined vital information contains a value determined to be an abnormal value by the determination unit;
   wherein intra-subject variation unique to the subject is reflected in vital information during at least 30 days; and
   wherein the normal distribution is created from the vital information during at least 30 days.

2. The system of claim 1, wherein the standard calculation unit is further configured to calculate a normal distribution from the mean $\mu$ and the standard deviation $\sigma$.

3. The system of claim 1, wherein standard calculation unit is configured to calculate the mean $\mu$ and the standard deviation $\sigma$ from at least two pieces of vital information recorded over a predetermined period on the information recording unit.

4. The system of claim 1, wherein the standard calculation unit is configured to calculates the mean $\mu$ and the standard deviation $\sigma$ from vital information recorded over at least 30 days on the information recording unit.

5. The system of claim 1, wherein the determination unit is configured to determine if the input predetermined vital information is an abnormal value, based on a lower limit and/or an upper limit,
   wherein the input predetermined vital information includes the vital information that was recently recorded on the information recording unit, and
   wherein the lower limit is a value of formula (1) below and the upper limit is a value of formula (2) below, wherein formula (1) is expressed by the mean $\mu$, the standard deviation $\sigma$, and n with n being greater than zero, and formula (2) is expressed by the mean $\mu$, the standard deviation $\sigma$, and m with m being greater than zero:

$$\mu - n\sigma \qquad \text{formula (1)}$$

$$\mu + m\sigma \qquad \text{formula (2)}$$

6. The system of claim 1, wherein the vital information contains values of the vital sign measured at least once in the morning and in the afternoon on the same day.

7. The system of claim 1, wherein the standard calculation unit configured to calculate at least one of the mean p and the standard deviation $\sigma$, in the multiple pieces of vital information recorded on the information recording unit, excluding vital information, of which a displacement from a value of the vital sign measured on the previous day exceeds a predetermined range.

8. The system of claim 1, further comprising a health inquiry information recording unit configured to allow first health inquiry information to be recorded together with an inquiry date information thereon, the first health inquiry information includes determinations of normality or abnormality for respective items as one or more inquiry results regarding the health condition of the subject,
   wherein, based on the first health inquiry information recorded on the health inquiry information recording unit, the standard calculation unit is configured to calculate the mean µ and/or the standard deviation σ of the multiple pieces of information recorded on the health inquiry information recording unit, excluding vital information measured on a day on which at least one determination of abnormality is recorded in the first health inquiry information recording unit.

9. The system of claim 1, wherein the standard calculation unit is further configured to calculate a recent vital mean value µ, which is a mean value of values of the vital sign for the last 7 days, and a comparison vital mean value, which is a mean value of values of the vital sign for the last 30 days, from the vital information recorded on the information recording unit;
   wherein the system further comprises a second determination unit; and
   wherein the second determination unit is configured to determine, as a value of condition deterioration tendency, if a difference between the recent vital mean value and the comparison vital mean value exceeds a predetermined range.

10. The system of claim 1, wherein, after the determination unit determines that the input predetermined vital information is an abnormal value, the information input unit receives re-measured vital information obtained from re-measurement performed on the subject and measurement date and time information thereof;
    wherein the information recording unit records the re-measured vital information and the measurement date and time information;
    wherein the system further comprises a third determination unit; and
    wherein the third determination unit is configured to determine whether or not the re-measured vital information is an abnormal value.

11. The system of claim 1, wherein the information recording unit allows target measurement time information to be recorded thereon wherein the target measurement time information corresponds to a target time to perform vital measurement; and
    wherein the standard calculation unit is configured to calculate the mean µ and/or the standard deviation σ of the multiple pieces of vital information recorded on the information recording unit, excluding vital information for which a time difference between the measurement date and time and the target measurement time information exceeds a predetermined range.

12. The system of claim 1, wherein the type of vital sign includes at least one selected from body temperature, pulse rate, systolic blood pressure, diastolic blood pressure, and respiration rate.

13. The system of claim 1, wherein the standard calculation unit is configured to calculate the mean µ and the standard deviation σ for a predetermined vital information wherein the predetermined vital information includes a set of measured values of the vital sign of the subject and the measurement date and time information recorded on the information recording unit.

14. The system of claim 1, wherein the information recording unit is further configured to record an individual identification information capable that includes an identification of subjects individually corresponding to the vital information of the subject on the information recording unit.

15. The system of claim 1, wherein the system is configured to measure the vital sign from a human being and/or an animal.

16. The system of claim 1, wherein the vital information comprises standard vital information and monitoring vital information,
    wherein the standard vital information includes a value of the vital sign measured before a predetermined measurement start time point and measurement date and time information thereof,
    wherein the monitoring vital information includes values of the vital sign measured multiple times during a predetermined time from the predetermined measurement start time point and measurement date and time information thereof, and
    wherein the standard calculation unit is configured to calculate the mean µ and/or the standard deviation σ of the vital information from at least one of the standard vital information and the monitoring vital information.

17. The system of claim 16, wherein the standard calculation unit is configured to calculate the mean µ and the standard deviation σ of the standard vital information and the monitoring vital information.

18. The system of claim 16, wherein the determination unit is configured to determine if an input determined vital information is an abnormal value based on a lower limit and/or upper limit,
    wherein the lower limit is a value of formula (1) below and the upper limit is a value formula (2) below, wherein formula (1) is expressed by the mean µ, the standard deviation σ, and n with n being greater than zero, and formula (2) is expressed by the mean µ, the standard deviation σ, and m with m being greater than zero:

$$\mu - n\sigma \qquad \text{formula (1)}$$

$$\mu + m\sigma \qquad \text{formula (2)}$$

19. The system of claim 16, wherein the system further comprises a health inquiry information recording unit configured to allow second health inquiry information to be recorded together with date information of the inquiry day thereon wherein the second health inquiry information includes determinations of normality or abnormality for respective items as a plurality of inquiry results regarding the health condition of the same subject,
    wherein, based on the second health inquiry information recorded on the health inquiry information recording unit, the standard calculation unit is configured to calculate the mean µ and/or the standard deviation σ in the multiple pieces of information recorded on the information recording unit, excluding vital information measured on a day on which at least one determination of abnormality from the second health inquiry information.

20. The system of claim 16, wherein the standard calculation unit is configured to calculate the mean µ and/or the standard deviation σ in the multiple pieces of vital information recorded on the information recording unit, excluding vital information with a displacement from a value of the vital sign measured on the previous day or before one timing exceeds a predetermined range.

21. A health condition determination apparatus for determining a health condition of a subject, based on vital information corresponding to a measured value of a vital sign, the health condition determination apparatus comprising:
- an information input unit configured to receive vital information following a normal distribution measured from the subject and measurement date and time information thereof;
- an information recording unit configured to allow the input vital information and measurement date and time information thereof to be recorded thereon;
- a standard calculation unit configured to calculate mean $\mu$ and/or standard deviation $\sigma$ of all or some of multiple pieces of the recorded vital information;
- a determination unit configured to determine whether or not the input vital information is an abnormal value, based on a predetermined numerical value set based on mean $\mu$ and/or the standard deviation $\sigma$; and
- a display unit configured to allow a determination result by the determination unit to be displayable thereon;
- wherein the predetermined numerical set is based on a normal distribution having the mean $\mu$ as a peak;
- wherein the vital information contains a value determined to be an abnormal value by the determination unit;
- wherein intra-subject variation unique to the subject is reflected in vital information during at least 30 days; and
- wherein the normal distribution is created from the vital information during at least 30 days.

22. The health condition determination apparatus of claim 21, the health condition determination apparatus further comprising a display information creation unit configured to create a body temperature table based on the vital information recorded on the information recording unit and create a normal distribution curve by graphing a probability density function of the normal distribution that is based on a normal distribution calculated from vital information during a predetermined period,
wherein the display unit is configured to allow the body temperature table and the normal distribution curve created by the display information creation unit to be displayable thereon.

23. A health condition determination method, as a method implemented by a computer, for determining a health condition of a subject, based on vital information corresponding to a measured value of a vital sign, the steps comprising:
- a step of calculating mean $\mu$ and/or standard deviation $\sigma$ of vital information during a predetermined number of days or more, in the vital information measured from the subject; and
- a step of determining if the input predetermined vital information is an abnormal value based on a predetermined numerical range set based on the mean $\mu$ and/or the standard deviation $\sigma$;
- wherein the predetermined numerical range is set based on a normal distribution having the mean $\mu$ as a peak;
- wherein the vital information contains a value determined to be an abnormal value by the determination unit;
- wherein intra-subject variation unique to the subject is reflected in vital information during at least 30 days; and
- wherein the normal distribution is created from the vital information during at least 30 days.

24. The health condition determination method of claim 23, wherein the determining step determines if the input predetermined vital information is an abnormal value based on a lower limit and/or an upper limit,
wherein the lower limit is a value of formula (1) below and the upper limit is a value of formula (2) below, wherein formula (1) is expressed by the mean $\mu$, the standard deviation $\sigma$, and n with n being greater than zero, and formula (2) is expressed by the mean $\mu$, the standard deviation $\sigma$, and m with m being greater than zero:

$$\mu - n\sigma \qquad \text{formula (1)}$$

$$\mu + m\sigma \qquad \text{formula (2)}$$

* * * * *